United States Patent
Dorr et al.

(10) Patent No.: US 6,514,726 B1
(45) Date of Patent: Feb. 4, 2003

(54) ASPERGILLUS FUMIGATUS ACETYL COENZYME-A CARBOXYLASE GENES AND POLYPEPTIDES AND USES THEREOF

(75) Inventors: Patrick K. Dorr, Sandwich (GB); Tanya Parkinson, Sandwich (GB); Christine Ellen Bulawa, Arlington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/475,252

(22) Filed: Dec. 30, 1999

Related U.S. Application Data

(60) Provisional application No. 60/114,580, filed on Dec. 31, 1998.

(51) Int. Cl.[7] .......................... C12N 15/09; C12P 21/06; C07H 21/04
(52) U.S. Cl. .................. 435/69.1; 435/320.1; 435/471; 435/325; 435/252.3; 435/254.3; 536/23.1
(58) Field of Search ................................ 435/69.1, 455, 435/471, 320.1, 325, 252.3, 254.3; 536/23.1

(56) References Cited

U.S. PATENT DOCUMENTS 5,925,805 A  * 7/1999 Ohlrogge et al. ........... 800/295

FOREIGN PATENT DOCUMENTS

| EP | 0 658 622 A2 | 12/1994 |
| FR | 2 727 129 | 11/1994 |

OTHER PUBLICATIONS

Database EMBL Online!, Barrell B.G. et al., Acetyl–CoA Carboxylase, XP002140927, abstract.
Morrice et al., "Isolation and characterization . . . ," Curr Genet, 34:379–385, 1998.

* cited by examiner

Primary Examiner—David Guzo
Assistant Examiner—Gerald G. Leffers, Jr.
(74) Attorney, Agent, or Firm—Fish & Richardson, P.C.

(57) ABSTRACT

Disclosed are *Aspergillus fumigatus* coenzyme-A carboxylase genes and polypeptides and their use in identifying antifungal agents, for example.

9 Claims, 4 Drawing Sheets

*A. fumigatus* ACCase
(SEQ ID NO:1)

GATTTTATCATGAAGTTGGCTGGCAATGCCCGGCATCTGGAAGTCCAGCTGCTGGCT
GATCAGTATGGAAACAACATCTCCCTGTTCGGCAGAGACTGCTCCGTACAGCGTCGT
CACCAGAAGATTATCGAGGAGGCCCCCGTCACCATCGCCAAGCCCGCCACGTTCCA
GGCCATGGAGCGTGCGGCTGTCAGCCTCGGAAAGCTGGTTGGTTACGTCTCCGCGGG
TACCGTCGAGTACCTGTACTCGCACGCCGATGACAAGTTCTACTTCCTCGAGTTGAA
CCCTCGTCTTCAGGTCGAGCACCCCACCACCGAAATGGTCTCCGGTGTCAACCTGCC
AGCCGCCCAATTGCAAATCGCCATGGGTATCCCTCTGCACCGCATCCGTGACATCCG
TCTGCTCTACGGGGTTGACCCCAACACCTCGTCCGAGATTGACTTCGACTTCTCCAG
CGAAGAGAGCTTCAAAACGCAGCGCCGCCCTCAGCCCAAGGGACACACGACCGCCT
GCCGTATCACTTCCGAAGATCCGGCGAAGGTTTCAAGCCCTCCAGCGGTACCATGC
ATGAATTGAACTTCCGCAGTTCGTCCAACGTCTGGGGTTACTTCTCCGTCGGTACCG
CCGGTGGTATCCACAGCTTCTCCGACAGCCAGTTCGGTCACATCTTTGCCTACGGTG
AGACGCGTTCCGCGTCGCGGAAACACATGGTTGTCGCTCTGAAGGAGTTGAGCATCC
GGGGTGACTTCCGCACGACAGTCGAGTACCTGATCAAGCTACTGGAGACCCCTGCTT
TCGAGGATAACACCATCACCACTGGATGGCTGGATCAGCTCATCTCGAACAAGCTG
ACCGCAGAGCGTCCGGATCCCATCGTGGCTGTTCTGTGCGGTGCGGTGACCAAGGCT
CACCTGGCCAGCGAAGGCGGTGTCGAGGAGTATCGCAAGGGCCTCGAAAAGGGTCA
GGTGCCCTCCAATGACGTCCTCAAGACCGTCTTCCCCGTGGACTTCATCTACGAGGG
CCAGCGGTACAAGTTCACCGCAACCAGAGCCGGCTTGGACAGCTACCACCTGTTCAT
CAACGGATCCAAGTGCTCGGTCGGTGTCCGTGCTCTGGCCGACGGTGGCCTGCTTGT
GCTCCTGAACGGTCGTAGTCACAACGTCTACTGGAAGGAGGAAGCGGCTGCAACTC
GCCTGAGTGTCGACGGAAAGACGTGCTTGCTGGAGCAGGAGAATGATCCTACTCAG
CTTCGCTCCCCGTCCCCGGAAAGCTTGTCAAGTTCACGGTCGAGAACGGCGAGCAC
GTCAAGGCTGGTCAGGCCTTCGCCGAAGTCGAGGTC<u>ATGAAGATG</u>¹TACATGCCCCT
GATTGCACAGGAAGATGGTATTGTTCAGCTCATCAAGCAGCCTGGTTCCACCCTCGA
GGCCGGTGACATCCTCGGTATTCTCGCTCTGGATGACCCATCTCGTGTCACACATGC
CCAGCCTTTTACCGGACAGCTGCCCGACCTTGGTCCCCGCAAGTGGTCGGTAACAA
GCCTCCTCAGAGATTCTCCCTCCTCCACAGTATTCTCGAGAACATCCTCATGGGCTAT
GACAACCAAGTTATCATGAACACCACTCTGAAGGAGCTGGTTGAGGTTTTGCGGGAT
CCTGAACTTCCCTACGGTGAATGGAACGCTCAGTCTTCTGCCCTTCATTCTCGTATGC
CCCAGAAGCTGGACGCTCAGCTTCAGAGCATCGTCGACAAGGCTCACGCCAGAAAG
GCCGAGTTCCCCGCCAAGCAGCTGCAGAAGACTATCTCCCGCTTCATCGAGGAGAA
CGTCAACCCAGCCGACGCCGAGATCCTCAAAACCACTCTCCTCCCTCTTCAGCAGGT
CATCACCAAGTACATGGATGGCCTGAAGGCCACGAGTTCAACGTCTTCGCTGGATT
GCTGGAGCAGTACTACAAGGTCGAGAGCCTCTTCTCTGGCCGCAACATCCGCGACG
AAGATGCCATCCTGAAGCTCAGAGAAGAGCACAAGGACGATATTGGCAGCGTCGTT
CAGCTGGTACTGTCCCACAGCCGTATTGGCGCGAAGAACAACCTCATTTTGGCCATC
CTGGCCATGTACCGCCCCAACCAGCCTGGTGCTGGCAATGTCGCAAAGTACTTCAAG
CCCGTCCTGAAGAAGCTCACTGAACTTGAGTCGCGGCCCGCCGCCAAGGTCACCCTC
AAGGCCCGTGAGGTCCTCATCCAGTGTGCGCTTCCCTCCATGGAGGAGCGTATGTCT
CAGATGGAACTCATTCTGCGCTCCTCTGTTGTCGAATCCCGATACGGAGAGACCGGT
TGGGACCACCGGGAGCCCGAATTCTCCGTCCTCAAGGAAGTGGTGGACTCCAAGTA

FIG. 1A

```
CACCGTCTTCGACGTCCTGACCCGATTCTTCGTTCATCCGGACCCTTGGGTCACCCTG
GCTGCTCTCGAGGTCTACATTCGCCGTGCCTACAGGGCCTATACACTGAAGGGTATT
CAGTACTACCCCGATGGAGAAGTCCCCCTGGTCTCCTGGGACTTTACGCTAGGCAAG
CTTGGACAACCGGAGTTCGGTTCCGTTCACTCCAACCAGATGTCTACGCCCAGCACA
CCTACTACGGAGTCCAACCCCTTCAGAAGACTCAACTCCATTAGTGATATGTCATAC
CTTGTCAACGACAGCAGCAATGAGCCCCTCAGAAAGGGTGTCATTGTTCCGGTTCAG
TCCCTGGAAGACGCCGAGGAGCAGCTGCCTAAGGCCTTGGAGGCACTCCCTCGTGC
CGGGTCGAAGAGGAAGCCGGGCGAGAACGGGCTGATTGCAGACCTGAGGGCAAGC
GTACCAGCCCCTCGCATTGAGTCGACAATTGAATTGACCGGTGTCTGCAACGTGGCT
GTCCGTGACCTCGAAGATCTTGACGACAACCAGATCGTTGCCCAGATCAACACCATT
CTTGCCGGCCTCAGGGACGAGTTGCTCGCTCGCCGCGTCCGCCGCGTGACCTTCATT
TGCGGCAAGGACGGCAGCTACCCTGGCTACTTCACCTTCCGTGGACCTACCTACGAG
GAAGATGAGAGCATCCGTCACAGCGAACCTGCGCTCGCCTTCCAGCTTGAACTCGG
ACGTCTGTCCAAATTCAAGATCAAGCCCGTCTTCACCGAGAACCGGAACATCCACGT
CTACGAGGCCATCGGCAAGGGCCCCGAGAACGACAACGCTGTCGACAAGCGTTACT
TCGTCCGTGCTGTGGTGCGCCCGGGCCGTCTCCGTGACGATATTCCCACCGCGGAGT
ACCTCATCTCCGAGGCTGACCGTCTCATGAATGACATTCTGGATGCCCTGGAGATCA
TCGGCAACAACAATTCTGATCCGAACCACATCTTCATCAACTTCTCGCCGGTGTTCA
ACCTGCAGCCCCAGGATGTGGAAGAGGCCTTGGCCGGTTTCCTTGAGCGCTTCGGTC
GCCGTCTCTGGCGTCTCCGTGTCACCGGTGCCGAGATCCGTATTCTATGCACCGATC
CTGCCACTGGCATGCCTTATCCTCTGCGTGTGATCATCACCAACACCTACGGCTTCAT
CATCCAGGTTGAGCTGTGCATTGAGAAGAAGTCCGAGAAGGGCGAGTGGCTCCTCC
ACAGCATCGGTGGTACCAACAAGCTCGGCTCGATGCACCTGCGTCCTGTCTCCACAC
CCTACCCGACCAAGGAGTGGCTTCAGCCCAAGCGTTACAAGGCTCATGTTATGGGC
ACCCAATACGTCTACGATTTCCCCGAATTGTTCCGACAGGCCTTCCAGAACAGCTGG
GCCAAGGCTGTAGCCAAGATCCCCTCCCTGGCCAGCAAGCGGCCCGCGGTTGGCGA
CTGCATTGAGTACAGCGAGCTTGTTCTCGATGATACCGACAACCTGATCGAAATCTC
GAGAGGCCCAGGTACCAACACCCACGGTATGGTTGGATGGATCGTTACCGCTCGCA
CCCCAGAGTATCCCGAAGGCCGACGGTTCATCATCGTTGCCAACGACATCACCTTCC
AGATCGGTTCCTTCGGTCCCCAGGAGGACAAGTTCTTCTACAAGTGTACCGAGTTGG
CCAGGAAGCTTGGAATCCCTCGTATCTACCTCTCAGCCAACTCCGGTGCTCGC²ATCG
GTATGGCCGACGAGCTGATCCCCTACTTCTCCGTGGCTTGGAACGACCCCCAGAAGC
CCGAGGCTGGATTCAAGTACCTTTACCTCACTCCCGAGGTCAAGCAAAAATTCGATG
CCAGTAAGAAGAAGGAGGTCATTACTGAGCTCATTCACGATGAGGGCGAAGAGCGC
CACAAGATTACGACTATCATTGGTGCTAAAGATGGCCTGGGTGTTGAGTGTCTGAAG
GGCTCTGGCCTCATCGCCGGAGCTACCTCGCGCGCTTACGAGGACATCTTCACCATC
ACCCTGGTCACCTGCCGCTCCGTTGGTATTGGTGCCTACCTTGTCCGTCTGGGCCAG
AGAGCCATCCAAGTAGAAGGCCAGCCGATTATTCTGACTGGTGCCCCGGCCATCAA
CAAGCTGTTGGGTCGCGAGGTTTACACATCTAACCTTCAGCTCGGTGGTACTCAGAT
CATGTACAAGAACGGTGTCTCTCACATGACTGCCACCGATGACTTTGAGGGGTGTCA
GAAGATTGTTGAGTGGATGTCCTTCGTTCCCGACAAGAAGGGTGCATCCATTCCCAT
CCTGCCCTGGTCCGATGACTGGGACCCGCGATGTCGCCTACTACCCTCTTCTAAGCA
GGCTTACGATGTCCGCTGGCTCATCGCTGGTAAAAAGGATGAGGAAGGCTTCCTCCC
TGGTCTGTTCGATGCCGGATCCTTTGAGGAGGCTCTTGGTGGATGGGCTCGTACCGT
TGTCGTTGGTCGTGCTCGCCTTGGTGGCATCCCTATGGGTGTAATTGCT³GTCGAGAC
TCGTTCGGTTGAGAACGTTACCCCTGCCGACCCTGCCAACCCTGACTCCATGGAGGT
```

FIG. 1B

```
GATCAGCCAGGAAGCCGGTGGTGTGTGGTACCCAAACTCGGCCTTCAAGACCGCTC
AGGCCCTCCGCGACTTCAATAATGGCGAGCAGCTGCCCGTCATGATTCTGGCCAACT
GGAGAGGCTTCTCCGGTGGCCAGCGTGACATGTACAACGAGGTTCTCAAGTACGGTT
CCTACATCGTCGATGCTCTGGTCAAGTACGAGCAGCCCATCTTCGTTTATATCCCAC
CTTTCGGTGAACTTCGTGGTGGTTCATGGGTCGTCATTGATCCCACGATCAACCCTG
ACCAGATGGAGATGTACGCTGATGAGGAGGCTCGCGGTGGTGTCCTCGAACCAGAA
GGTATCGTGAACATCAAGTACCGCCGTGAGAAGCAGCTCGACACTATGGCTCGTCTC
GACGCCACGTACGGCGAGCTCCGTCGTGCTCTTGAGGACCCATCCCTCAGCAAGGA
GCAGCTCTCAGAGATCAAGGCCAAGATGGCCGCTCGCGAAGAGCAGCTCCTcCCTGT
CTACCTGCAGATCGCTCTGCAATTTGCTGATCTTCACGACCGCGCTGGCCGCATGGT
GGCCAAGAATACCATCCGCAAGGCCCTGACCTGGAAGAACGCCAGACGCTTCTTCT
ACTGGCGTGTACGCCGCCGCTTGAGCGAGGAGCTCATTCTCAAGCGCATGGCCTCTG
CcGCCCCGGCCGCCGTCTCCGGCGAGGCCACCGGCGCCATCCCTGCCACCGGACTCG
TCGACGGCCAGACCCCATCCAATGAGAGCCCTCGCGCTAAGCACCTGCGCACCCTG
CACTCGTGGACCGGCTTCCTGGACGAGGAACTCGAGCACGACGACCGCAAGGTAGC
CATGTGGTACGAGGAGAACAGAAAGGCCATCCAGATGAAGATCGAGGCCCTTAAGA
CCGACTCTGTCGCCACCGAGATCGCCCAGCTGCTCATCAGCAACAAGGAGGGCGGT
CTCAAGGGTGTGCAGCAAGTTCTCAGCATGCTGCCTGTGAGGAGAAGGAGCCCGGT
GCTCAAGTACCTTGGGCTCACCATGAAAATAGAATGAAACATAGAACCGCCCGGT
GCATATCTTTTGTTCCCCCCCCCCTTTACTGGATTATATTTTCCAAATTCCTGATCAC
ATTACGGTACATTGAAGATGGCTTTATACAAGGCGGGTGCGTTAGGGTCTGTGTTTT
GTTTGTCTGCACTACGGTTTTGCGTTTTTGTCTTGCATGGGTCTTGGAGGTTGCATCG
GCTGATTACTATTGTATGCATTATGTTGGTATGCCTGATGTTCTCTGGCAATGTTTCT
ATTCACTTTTTCCTAGCAATGCCAATGAATCTTCGACTTCAAAAAAAAAAAAAAAAA
```

1- biotin binding (bp 1342-1350)
2- carboxybiotin domain (bp 3982-4137)
3- acetyl coA binding (bp 4810-4929)
TGA-STOP (bp 6046)

FIG. 1C (SEQ ID NO:2)
DFIMKLAGNARHLEVQLLADQYGNNISLFGRDCSVQRRHQKIIEEAPVTIAKPATFQAM
ERAAVSLGKLVGYVSAGTVEYLYSHADDKFYFLELNPRLQVEHPTTEMVSGVNLPAAQ
LQIAMGIPLHRIRDIRLLYGVDPNTSSEIDFDFSSEESFKTQRRPQPKGHTTACRITSEDPG
EGFKPSSGTMHELNFRSSSNVWGYFSVGTAGGIHSFSDSQFGHIFAYGETRSASRKHMV
VALKELSIRGDFRTTVEYLIKLLETPAFEDNTITTGWLDQLISNKLTAERPDPIVAVLCGA
VTKAHLASEGGVEEYRKGLEKGQVPSNDVLKTVFPVDFIYEGQRYKFTATRAGLDSYH
LFINGSKCSVGVRALADGGLLVLLNGRSHNVYWKEEAAATRLSVDGKTCLLEQENDPT
QLRSPSPGKLVKFTVENGEHVKAGQAFAEVEVMKMYMPLIAQEDGIVQLIKQPGSTLEA
GDILGILALDDPSRVTHAQPFTGQLPDLGPPQVVGNKPPQRFSLLHSILENILMGYDNQVI
MNTTLKELVEVLRDPELPYGEWNAQSSALHSRMPQKLDAQLQSIVDKAHARKAEFPAK
QLQKTISRFIEENVNPADAEILKTTLLPLQQVITKYMDGLKAHEFNVFAGLLEQYYKVES
LFSGRNIRDEDAILKLREEHKDDIGSVVQLVLSHSRIGAKNNLILAILAMYRPNQPGAGN
VAKYFKPVLKKLTELESRPAAKVTLKAREVLIQCALPSMEERMSQMELILRSSVVESRY
GETGWDHREPEFSVLKEVVDSKYTVFDVLTRFFVHPDPWVTLAALEVYIRRAYRAYTL
KGIQYYPDGEVPLVSWDFTLGKLGQPEFGSVHSNQMSTPSTPTTESNPFRRLNSISDMSY
LVNDSSNEPLRKGVIVPVQSLEDAEEQLPKALEALPRAGSKRKPGENGLIADLRASVPAP
RIESTIELTGVCNVAVRDLEDLDDNQIVAQINTILAGLRDELLARRVRRVTFICGKDGSYP
GYFTFRGPTYEEDESIRHSEPALAFQLELGRLSKFKIKPVFTENRNIHVYEAIGKGPENDN
AVDKRYFVRAVVRPGRLRDDIPTAEYLISEADRLMNDILDALEIIGNNNSDPNHIFINFSP
VFNLQPQDVEEALAGFLERFGRRLWRLRVTGAEIRILCTDPATGMPYPLRVIITNTYGFII
QVELCIEKKSEKGEWLLHSIGGTNKLGSMHLRPVSTPYPTKEWLQPKRYKAHVMGTQY
VYDFPELFRQAFQNSWAKAVAKIPSLASKRPAVGDCIEYSELVLDDTDNLIEISRGPGTN
THGMVGWIVTARTPEYPEGRRFIIVANDITFQIGSFGPQEDKFFYKCTELARKLGIPRIYLS
ANSGARIGMADELIPYFSVAWNDPQKPEAGFKYLYLTPEVKQKFDASKKKEVITELIHD
EGEERHKITTIIGAKDGLGVECLKGSGLIAGATSRAYEDIFTITLVTCRSVGIGAYLVRLG
QRAIQVEGQPIILTGAPAINKLLGREVYTSNLQLGGTQIMYKNGVSHMTATDDFEGCQKI
VEWMSFVPDKKGASIPILPWSDDWDPRCRLLPSSKQAYDVRWLIAGKKDEEGFLPGLFD
AGSFEEALGGWARTVVVGRARLGGIPMGVIAVETRSVENVTPADPANPDSMEVISQEA
GGVWYPNSAFKTAQALRDFNNGEQLPVMILANWRGFSGGQRDMYNEVLKYGSYIVDA
LVKYEQPIFVYIPPFGELRGGSWVVIDPTINPDQMEMYADEEARGGVLEPEGIVNIKYRR
EKQLDTMARLDATYGELRRALEDPSLSKEQLSEIKAKMAAREEQLLPVYLQIALQFADL
HDRAGRMVAKNTIRKALTWKNARRFFYWRVRRRLSEELILKRMASAAPAAVSGEATG
AIPATGLVDGQTPSNESPRAKHLRTLHSWTGFLDEELEHDDRKVAMWYEENRKAIQMK
IEALKTDSVATEIAQLLISNKEGGLKGVQQVLSMLPVRRRSPVLKYLGLTMKIE

FIG. 2

ASPERGILLUS FUMIGATUS ACETYL COENZYME-A CARBOXYLASE GENES AND POLYPEPTIDES AND USES THEREOF

CROSS-REFERENCE TO RELATED APPLICATION

This application claims priority under 35 U.S.C. §119 from U.S. Ser. No. 60/114,580, filed Dec. 31, 1998.

FIELD OF THE INVENTION

The invention relates to acetyl coenzyme A carboxylase genes of the fungus *Aspergillus fumigatus* and their use in identifying antifungal agents.

BACKGROUND OF THE INVENTION

The enzyme acetyl coenzyme A carboxylase (ACCase) is responsible for synthesizing malonyl CoA from acetyl CoA. ACCase is essential for synthesis of fatty acids.

By way of background, the Fungi Kingdom consists of two divisions, the Eumycota and Myxomycota or the true fungi and slime molds, respectively. The true fungi are those species that are hyphal or are clearly related to species that are hyphal, possess cell walls throughout most or all of their life cycle, and are exclusively absorptive in their function. The slime molds are organisms that do not form hyphae, lack cell walls during the phase in which they obtain nutrients and grow and are capable of ingesting nutrients in particulate form by phagocytosis.

The two most important classes of true fungi in which most species produce motile cells, known as zoospores, are the Oomycetes, and the Chytridiomycetes. The fungi that lack zoospores are classified according to the sexual phase of the fungal life cycle. The sexual process leads to the production of characteristic spores in the different groups. The fungi that form zygospores are classified as Zygomycetes, those that form ascospores are classified as Ascomycetes, and those forming basidiospores are classified as Basidiomycetes. There are also many species, recognizable as higher fungi through the presence of cell walls in their hyphae, that produce asexual spores but lack a sexual phase. These are known as Deuteromycetes, and details of their asexual sporulation are used to classify them. A representative member of the Deuteromycetes includes *Candida albicans*. These species are extensively reviewed in "The Fungi" (Ed M J Carlile and S C Watkinson 1994 Acad Press Ltd) and "The Growing Fungus" (Ed. N A R Gow and G M Gadd, 1995, Chapman and Hall).

Yeast are fungi that are normally unicellular and reproduce by budding although some will, under appropriate conditions, produce hyphae, just as some normally hyphal fungi may produce a yeast phase. The best known of all yeasts is *Saccharomyces cerevisiae,* which is a member of the Ascomycetes species. It is commonly regarded as a diploid yeast since mating usually soon follows ascospore germination. However, single cells can be used to establish permanently haploid cultures.

Fungal and other mycotic pathogens are responsible for a variety of diseases in humans, animals and plants. Fungal infection is also a significant problem in veterinary medicine. Some of the fungi that infect animals can be transmitted from animals to humans. Fungal infections or infestations are also a very serious problem in agriculture with fungicides being employed to protect vegetable and fruit and cereal crops. Fungal attack of wood products is also of major economic importance. Additional products that are susceptible to fungal infestation include textiles, plastics, paper and paint. Some of these fungal targets are extensively reviewed in WO 95/11969.

Statistics show that the incidence of fungal infections has doubled from the 1980's to the 1990's, and infections of the blood stream have increased fivefold with an observed mortality of 50% (Tally et al., 1997, Int. Conference Biotechnol Microb. Prods: Novel Pharmacol. Agrobiol. Activities, Williamsburg, Va. Abstr S5 p19). These include those fungal infections, such as candidiasis, to which all individuals are susceptible, but also infections such as cryptococcosis and aspergillosis, which occur particularly in patients of compromised immune status.

By way of example, the yeast *Candida albicans* (*C. albicans*) has been shown to be one of the most pervasive fungal pathogens in humans. It has the capacity to opportunistically infect a diverse spectrum of compromised hosts, and to invade many diverse tissues in the human body. It can in many instances evade antibiotic treatment and the immune system. Although *Candida albicans* is a member of the normal flora of the mucous membranes in the respiratory, gastrointestinal, and female genital tracts, in such locations, it may gain dominance and be associated with pathologic conditions. Sometimes it produces progressive systematic disease in debilitated or immunosuppressed patients, particularly if cell-mediated immunity is impaired. Sepsis may occur in patients with compromised cellular immunity, e.g., those undergoing cancer chemotherapy or those with lymphoma, AIDS, or other conditions. Candida may produce bloodstream invasion, thrombophlebitis, endocarditis, or infection of the eyes and virtually any organ or tissue when introduced intravenously, e.g., via tubing, needles, narcotics abuse etc.

*Candida albicans* has been shown to be diploid with balanced lethals, and therefore probably does not go through a sexual phase or meiotic cycle. This yeast appears to be able to spontaneously and reversibly switch at high frequency between at least seven general phenotypes. Switching has been shown to occur not only in standard laboratory strains, but also in strains isolated from the mouths of healthy individuals.

Nystatin, ketoconazole, and amphotericin B are drugs that have been used to treat oral and systemic Candida infections. However, orally administered nyastin is limited to treatment within the gut and is not applicable to systemic treatment. Some systemic infections are susceptible to treatment with ketoconazole or amphotericin B, but these drugs may not be effective in such treatment unless combined with additional drugs. Amphotericin B has a relatively narrow therapeutic index and numerous undesirable side effects, ranging from nausea and vomiting to kidney damage and toxicities occur even at therapeutic concentrations. While ketoconazole and other azole antifungals exhibit significantly lower toxicity, their mechanism of action, through inactivation of cytochrome $P_{450}$ prosthetic group in certain enzymes (some of which are found in humans) precludes use in patients that are simultaneously receiving other drugs that are metabolized by the body's cytochrome $P_{450}$ enzymes. These adverse effects mean that their use is generally limited to the treatment of topical or superficial infections. In addition, resistance to these compounds is emerging and may pose a serious problem in the future. The more recently developed triazole drugs, such as fluconazole, are believed by some to have fewer side effects but are not completely effective against all pathogens.

Invasive aspergillosis, caused by *Aspergillus fumigatus* (*A. fumigatus*) has also become an increasingly opportunistic infection. There has been a 14-fold increase in its incidence during the past 12 years as detected by autopsy, and only two drugs are available that are effective in its treatment, neither of which is completely satisfactory. Amphotericin B needs to be given intravenously and has a number of toxic side effects. Itraconazole, which can be given orally is often prescribed imprudently, encouraging the emergence of resistant fungal strains (Dunn-Coleman and Prade, Nature Biotechnology, 1998, 16: 5). Resistance is also developing to synthetic azoles (such as fluconazole and flucytosine), and the natural polyenes (such as amphotericin B) are limited in use by their toxicity.

Fungicide resistance generally develops when a fungal cell or fungal population that originally was sensitive to a fungicide becomes less sensitive by heritable changes after a period of exposure to the fungicide.

In certain applications, such as agriculture, it is possible to combat resistance through alteration of fungicides or the use of fungicide mixtures. To prevent or delay the build up of a resistant pathogen population, different agents that are effective against a particular disease must be available. One way of increasing the number of available agents is to search for new site-specific inhibitors.

Consequently, antifungal drug discovery efforts have been directed at components of the fungal cell or its metabolism that are unique to fungi, and hence might be used as therapeutic targets of new agents which act on the fungal pathogen without undue toxicity to host cells. Such potential targets include enzymes critical to fungal cell wall assembly (U.S. Pat. No. 5,194,600) as well as topoisomerases (enzymes required for replication of fungal DNA). Two semisynthetic antifungal agents such as the echinocandins and the related pneumocandins are in late stage clinical trials. Both are cyclic lipopeptides produced by fungi that non-competitively inhibit (1,3)-glucan synthase and thus interfere with the biosynthesis of the fungal cell wall. These clinical candidates are generally more water-soluble, have improved pharmacokinetics and broader antifungal spectra than their natural parent compounds and have activity spectra that include many Candida species, including *Candida albicans,* and Aspergilli.

Because no single approach may be effective against all fungal pathogens, however, and because of the possibility of developed resistance to previously effective antifungal compounds, there remains a need for new antifungal agents with novel mechanisms of action and improved or different activity profiles. There is also a need for agents which are active against fungi but are not toxic to mammalian cells, as toxicity to mammalian cells can lead to a low therapeutic index and undesirable side effects in the host (e.g., patient). An important aspect of meeting this need is the selection of an appropriate component of fungal structure or metabolism as a therapeutic target.

Even after a particular intracellular target is selected, the means by which new antifungal agents are identified pose certain challenges. Despite the increased use of rational drug design, a preferred method continues to be the mass screening of compound "libraries" for active agents by exposing cultures of fungal pathogens to the test compounds and assaying for inhibition of growth. In testing thousands or tens of thousands of compounds, however, a correspondingly large number of fungal cultures must be grown over time periods which are relatively long compared to most bacterial culture times. Moreover, a compound which is found to inhibit fungal growth in culture may be acting not on the desired target but on a different, less unique fungal component, with the result that the compound may act against host cells as well and thereby produce unacceptable side effects. Consequently, there is a need for an assay or screening methods which more specifically identifies those agents that are active against a certain intracellular target. Additionally, there is a need for assay methods having greater throughput, that is, assay methods which reduce the time and materials needed to test each compound of interest.

Although cyclic lipopeptides produced by fungi are in late-stage clinical trials as potential anti-fungal agents, the lipid biosynthesis and degradation pathways have been only sparingly investigated in fungi. This area is reviewed by Weete (1980 Lipid Biochemistry of Fungi and Other Organisms, Plenum New York) and Chopra and Khuller (1984 Crit Rev Microbiol 11: 209–250). It is known that fungal biosynthesis of fatty acids takes place in the cytosol and starts with carboxylation of acetyl-CoA to malonyl-CoA. From this malonyl-CoA consecutive C2 units are added to acetyl-CoA or the growing fatty-CoA ester chain by a complex fatty acid synthase complex harboring seven different enzymatic activities. In contrast, knowledge of lipid biosynthesis and degradation has come from research in other organisms.

By way of example, it has been recognized that the biosynthesis of very long chain fatty acids in organisms other than fungi requires four enzyme systems: acetyl coenzyme A (CoA) carboxylase, fatty acid synthetase, fatty acid desaturase, and fatty acyl chain elongation system. The rate limiting step of the de novo synthesis of fatty acids is under the control of the first of these, acetyl-CoA carboxylase (EC 6.4.1.2). This enzyme catalyses the ATP-dependent carboxylation of acetyl CoA to yield malonyl CoA which serves as the two carbon unit donor for the subsequent synthesis of long chain fatty acids by the fatty acid synthase complex. The chain length of newly synthesized fatty acids appears to depend on the concentration of malonyl-CoA rather than on the activity of the fatty acid synthase complex. Acetyl-CoA carboxylase thus regulates both the overall rate of de novo synthesis and chain length distribution of long chain fatty acids.

Acetyl-CoA carboxylase has been isolated from chicken liver (Buckner and Kolattakudy 1976 Biochem 15: 1948–1957; Manning et al 1976 Biochem J 153: 463–468; Ahmad et al 1978 J Biol Chem 253: 1733–1737; Hardie and Cohen 1978 FEBS Lett 91: 1–7); rat heart (Thampy 1989 J Biol Chem 264: 17631–17634); brown and white adipose tissue (Bianchi et al 1990 J Biol Chem 265: 1502–1509; Iverson et al 1990 Biochem J 269: 365–371); chick embryo brain (Thampy and Koshy 1991 J Lipid Res 32: 1667–1673) and has been observed by immunological techniques in rat diaphragm muscle (Bianchi et al 1990 ibid). Acetyl-CoA carboxylase has also been found in human skeletal muscle and adipose tissue (Witters et al 1994 Int J Biochem 26: 589–594) and in rat skeletal muscle (Trumble et al 1991 Life Sci 49: 39–43).

Data have been accumulating from several laboratories characterizing the different isoforms of Acetyl-CoA carboxylase. Thampy (1989 ibid) and Bianchi et al (1990 ibid) have reported a molecular mass of 280 kDa for the Acetyl-CoA carboxylases from rat heart and diaphragm muscle respectively. More recently, two isoforms (HACC275 and HACC 265) have been identified in human tissue. The HACC 275 form is predominant in human skeletal muscle (Witters et al 1994 ibid). The rat skeletal muscle isoform appears to be similar in molecular mass to the HACC 275 form in humans. However, it has been recognized that until the Acetyl-CoA carboxylase gene(s) from each tissue are cloned and the mRNA species are characterized, assumption of equivalency of isoforms with molecular masses is conjectural (Trumble et al 1995 Eur J Biochem 231: 192–198).

Preliminary studies on Acetyl-CoA carboxylase (Acc1p) from yeast Saccharomyces has been shown to: (i) have a subunit molecular mass of 250 kDa, (ii) be active as a tetramer and (iii) be subject to short term regulation by phosphorylation (Al-Feel et al 1992 Proc Natl Acad Sci 89: 4534–4538; Obernayer and Lynen 1976: Trends Biochem Sci 1: 169–171; Witters et al 1990 Biochem Biophys Res Commun 169: 369–376). Genetic and biochemical analyses of fatty acid synthesis mutants and a conditional mRNA transport mutant of *Saccharomyces cerevisiae*, acc1-7-1, have also indicated that the continued synthesis of malonyl-CoA, the enzymatic product of acetyl-CoA carboxylase, is an essential function of the acetyl-CoA carboxylase (ACC1) gene (Schneiter et al 1996 Mol and Cell Biol 16: 7161–7172).

SUMMARY OF THE INVENTION

The invention is based on the discovery of an ACCase gene (afACC1) in the fungus *Aspergillus fumigatus*, which is essential for survival. Essential genes are genes which are required for growth (such as metabolism, division, or reproduction) and survival of an organism. Essential genes can be used to identify therapeutic antifungal agents. These therapeutic agents can reduce or prevent growth, or decrease pathogenicity or virulence, and preferably, kill the organism.

The *A. fumigatus* ACCase (afACCase) coding sequence is depicted in FIGS. 1A–C as SEQ ID NO:1, and the amino acid sequence is depicted in FIG. 2 as SEQ ID NO:2. Thus the present invention relates to a novel ACCase enzyme—which is specific to *A. fumigatus*—and to a nucleotide sequence (afACC1) encoding same. The present invention also relates to the use of the novel nucleic acid and amino acid sequences in the diagnosis and treatment of disease. The present invention also relates to the use of the novel nucleic acid and amino acid sequences to evaluate and/or to screen for agents that can modulate ACCase activity. The present invention further relates to genetically engineered host cells that include or express the novel nucleic acid and amino acid sequences to evaluate and/or to screen for agents that can modulate ACCase activity.

The ACCase enzyme of the present invention is obtainable from the *A. fumigatus* fungal species. This ACCase enzyme is distinguishable from the Acetyl-CoA carboxylase enzymes identified in human skeletal and adipose tissue and the yeast (*S. cerevisiae*) Acetyl-CoA carboxylase known as Acc1p.

The ACCase enzyme of the present invention may be the same as the naturally occurring form—for this aspect, e.g., the ACCase can be the non-native amino acid sequence—or a variant, homolog, fragment or derivative thereof. In addition, or in the alternative, the ACCase is isolated ACCase and/or purified ACCase. The ACCase can be obtainable from or produced by any suitable source, whether natural or not, or it may be synthetic, semi-synthetic or recombinant.

The ACCase gene of the invention is essential for survival of *A. fumigatus*. Accordingly, the ACCase nucleic acid sequence of the invention, and the ACCase polypeptide of the invention, are useful targets for identifying compounds that are inhibitors of *A. fumigatus*. Such inhibitors attenuate fungal growth by inhibiting the activity of the ACCase polypeptide, or by inhibiting transcription or translation. Accordingly, in one aspect, this invention provides isolated nucleic acid molecules encoding *A. fumigatus* ACCase polypeptides or biologically active portions thereof, as well as nucleic acid fragments suitable as primers or hybridization probes for the detection of ACCase-encoding nucleic acids (e.g., fragments of at least 15 nucleotides (e.g., at least 18, 20, or 25 nucleotides)).

The invention features a nucleic acid molecule that is at least 65% (or 75%, 85%, 95%, 98%, or 100%) identical to the nucleotide sequence shown in SEQ ID NO:1, or the nucleotide sequence of the cDNA insert of the plasmid deposited with the ATCC (10801 University Blvd., Manassas, Va. 209110-2209, USA) on Dec. 15, 1998 as Accession Number 207005, 207006, 207007, 207008, or 207009 (the "cDNA of ATCC 207005, 207006, 207007, 207008, or 207009"), or a complement thereof. The deposited biological samples contain *E. coli* cells containing the plasmid EpAFACC-1, EpAFACC-2, EpAFACC-3, EpAFACC-4, and EpAFACC-5, respectively. Each EpAFACC plasmid contains a partial cDNA sequence of *A. fumigatus* ACCase, with the five plasmids together providing a complete cDNA sequence of *A. fumigatus* ACCase.

The invention features a nucleic acid molecule that includes a fragment of at least 300 (e.g., 325, 350, 375, 400, 425, 450, 500, 550, 600, 650, 700, 800, 900, 1000, 1200, 1400, 1600, or 1770) nucleotides of the nucleotide sequence shown in SEQ ID NO:1, or the nucleotide sequence of the cDNA ATCC 207005, 207006, 207007, 207008, or 207009, or a complement thereof.

The invention also features a nucleic acid molecule that includes a nucleotide sequence encoding a protein having an amino acid sequence that is at least 65% (or 75%, 85%, 95%, 98%, or 100%) identical to the amino acid sequence of SEQ ID NO:2 or the amino acid sequence encoded by the cDNA of ATCC 207005, 207006, 207007, 207008, or 207009.

Also within the invention is a nucleic acid molecule that encodes a fragment of a polypeptide having the amino acid sequence of SEQ ID NO:2, the fragment including at least 15 (25, 30, 50, 100, 150, 300, 400, or 450) contiguous amino acids of SEQ ID NO:2 or the polypeptide encoded by the cDNA of ATCC Accession Number 207005, 207006, 207007, 207008, or 207009.

In other embodiments, the invention features an isolated ACCase protein having an amino acid sequence that is at least about 65% (e.g., 75%, 85%, 95%, 98%, or 100%) identical to the amino acid sequence of SEQ ID NO:2; and an isolated ACCase protein which is encoded by a nucleic acid molecule having a nucleotide sequence that is at least about 65% (e.g., 75%, 85%, 95%, or 100%) identical to SEQ ID NO:1 or the cDNA of ATCC 207005, 207006, 207007, 207008, or 207009; and an isolated ACCase protein which is encoded by a nucleic acid molecule having a nucleotide sequence which hybridizes under stringent hybridization conditions to a nucleic acid molecule having the nucleotide sequence of SEQ ID NO:1 or the non-coding strand of the cDNA of ATCC 207005, 207006, 207007, 207008, or 207009.

Another embodiment of the invention features ACCase nucleic acid molecules that specifically detect *A. fumigatus* ACCase nucleic acid molecules relative to nucleic acid molecules encoding other ACCases. For example, in one embodiment, an *A. fumigatus* ACCase nucleic acid molecule hybridizes under stringent conditions to a nucleic acid molecule that includes the nucleotide sequence of SEQ ID NO:1, or the cDNA of ATCC 207005, 207006, 207007, 207008, or 207009, or a complement thereof. In another embodiment, the *A. fumigatus* ACCase nucleic acid molecule is at least 300 (e.g., 400, 500, 700, 900, 1100, or 1300) nucleotides in length and hybridizes under stringent conditions to a nucleic acid molecule that includes the nucleotide sequence shown in SEQ ID NO:1, the cDNA of ATCC 207005, 207006, 207007, 207008, or 207009, or a complement thereof. In another embodiment, the invention provides an isolated nucleic acid molecule which is antisense to the coding strand of an *A. fumigatus* ACCase nucleic acid.

Another aspect of the invention provides a vector, e.g., a recombinant expression vector, that includes an ACCase nucleic acid molecule of the invention. In another embodiment the invention provides a host cell containing such a vector. The invention also provides a method for producing ACCase protein by culturing, in a suitable medium, a host cell of the invention containing a recombinant expression vector such that an ACCase protein is produced.

Another aspect of this invention features isolated or recombinant ACCase proteins and polypeptides. Typical ACCase proteins and polypeptides possess at least one biological activity possessed by naturally occurring *A. fumigatus* ACCase, e.g., an ability to synthesize malonyl CoA from acetyl CoA. It is not necessary that the ACCase polypeptide have activity that is equivalent to that of the wild-type *A. fumigatus* ACCase. For example, the ACCase polypeptide can have 20, 50, 75, 90, 100, or an even higher percent of the wild-type activity.

Since the *A. fumigatus* ACCase gene, which is essential for survival, has been identified, nucleic acids encoding *A. fumigatus* ACCase and *A. fumigatus* ACCase proteins can be used to identify antifungal agents. Such antifungal agents can be identified with high throughput assays to detect inhibition of ACCase activity. For example, this inhibition can be caused by small molecules binding directly to the ACCase polypeptide or by binding of small molecules to other essential polypeptides in a biochemical pathway in which ACCase participates.

The invention also provides methods of identifying agents (such as compounds, other substances, or compositions) that affect, or selectively affect, (such as inhibit or otherwise modify) the activity of and/or expression of the ACCase, by contacting the ACCase or the nucleotide sequence coding for same with the agent and then measuring the activity of the ACCase and/or the expression thereof. In a related aspect, the invention features a method of identifying agents (such as compounds, other substances or compositions comprising same) that affect (such as inhibit or otherwise modify) the activity of and/or expression of afACCase, by measuring the activity of and/or expression of afACCase in the presence of the agent or after the addition of the agent in: (a) a cell line into which has been incorporated a recombinant construct including the nucleotide sequence of the afACCase gene (e.g., SEQ ID NO:1) or an allelic variation thereof, or (b) a cell population or cell line that naturally selectively expresses afACCase, and then measuring the activity of afACCase and/or the expression thereof.

Since the *Aspergillus fumigatus* ACCase gene has been identified, it can be cloned into various host cells (e.g., fungi, *E. coli* or yeast) for carrying out such assays in whole cells). Similarly, conventional in vitro assays of ACCase activity can be used with the ACCase of the invention.

In one embodiment, the invention features a method for identifying a compound for the treatment of a fungal infection, wherein the method entails, in sequence, (i) preparing a first cell and a second cell, the first and second cells being capable of expressing afACCase, (ii) contacting the first cell with a test compound, (iii) determining the level of expression of afACCase in the first and second cells, (iv) comparing the level of expression in the first cell with the second cell, and (v) selecting the test compound for treatment of a fungal infection where expression of afACCase in the first cell is less than expression of the essential gene in the second cell, and wherein the afACCase gene is a first nucleic acid molecule which encodes a polypeptide including the amino acid sequence of SEQ ID NO: 2, or a naturally occurring allelic variant thereof, and wherein the first nucleic acid molecule hybridizes under stringent conditions to a second nucleic acid molecule, the second nucleic acid molecule consisting of a nucleotide sequence of SEQ ID NO: 1. The determination of the level of expression of the afACCase gene can be made by measuring the amount of mRNA transcribed from the afACCase gene. Alternatively, the level of afACCase encoded by the afACCase gene can be measured.

The test compound can be a small organic molecule. Alternatively, the test compound can be a test polypeptide (e.g., a polypeptide having a random or predetermined amino acid sequence; or a naturally-occurring or synthetic olypeptide) or a nucleic acid, such as a DNA or RNA molecule. The test compound can be a naturally-occurring compound or it can be synthetically produced. Synthetic libraries, chemical libraries, and the like can be screened to identify compounds that bind to ACCase.

In another suitable method, there is provided an assay method for identifying an agent that can affect Acetyl CoA Carboxylase (ACC) activity or expression thereof, the assay method comprising contacting an agent with an amino acid sequence according to the present invention or a nucleotide sequence according to the present invention; and measuring the activity or expression of ACC; wherein a difference in activity between a) ACCase activity or expression in the absence of the agent and b) ACCase activity or expression in the presence of the agent is indicative that the agent can affect ACCase activity or expression.

Another suitable method for identifying antifungal compounds involves screening for small molecules that specifically bind to ACCase. A variety of suitable binding assays are known in the art as described, for example, in U.S. Pat. Nos. 5,585,277 and 5,679,582, hereby incorporated herein by reference. For example, in various conventional assays, test compounds can be assayed for their ability to bind a polypeptide by measuring the ability of the small molecule to stabilize the polypeptide in its folded, rather than unfolded, state. More specifically, one can measure the degree of protection against unfolding that is afforded by the test compound. Test compounds that bind afACCase with high affinity cause, for example, a significant shift in the temperature at which the polypeptide is denatured. Test compounds that stabilize the polypeptide in a folded state can be further tested for antifungal activity in a standard susceptibility assay.

In a related method for identifying antifungal compounds, an ACCase polypeptide is used to isolate peptide or nucleic acid ligands that specifically bind to the ACCase polypeptides. These peptide or nucleic acid ligands are then used in a displacement screen to identify small molecules that bind to the ACCase polypeptide. Such binding assays can be carried out as described herein.

The *A. fumigatus* ACCase polypeptides also can be used in assays to identify test compounds that bind to the polypeptides. Test compounds that bind to the ACCase polypeptides then can be tested, in conventional assays, for their ability to inhibit fungal growth. Test compounds that bind to the ACCase polypeptides are candidate antifungal agents, in contrast to compounds that do not bind to the ACCase polypeptides. As described herein, any of a variety of art-known methods can be used to assay for binding of test compounds to the ACCase polypeptides.

The invention includes, for example, a method for identifying a compound useful for treating a fungal infection, wherein the method entails (a) measuring the level of expression of the afACCase gene in a cell in the presence of a test compound; (b) comparing the level of expression measured in step (a) to the level of expression of the afACCase gene in a cell in the absence of the test compound; and (c) selecting the test compound as being useful for treating a fungal infection when the level of expression of the afACCase gene in the presence of the test compound is less than the level expression of the afACCase gene in the absence of the test compound, and wherein the afACCase gene has the sequence of SEQ ID NO: 1. If desired, the level of expression can be measured by measuring the amount of mRNA from the afACCase gene described herein, or by measuring the amount of protein encoded by the afACCase gene described herein. Typically, the cell is A. fumigatus or Saccharomyces (e.g., Saccharomyces cerevisiae).

In a variation of the above method, the invention features a method for identifying a compound useful for treating a fungal infection, wherein the method entails (a) measuring the activity of the afACCase gene in a cell in the presence of a test compound; (b) comparing the activity measured in step (a) to the level activity of the afACCase gene in a cell in the absence of the test compound; and (c) selecting the test compound as being useful for treating fungal infections when the level of activity of the afACCase gene measured in the presence of the test compound is less than the level of activity of the afACCase gene measured in the absence of the test compound, wherein the afACCase gene has the sequence of SEQ ID NO: 1.

In an alternative method, the invention features a method for identifying a compound useful for treating a fungal infection, wherein the method entails (a) measuring, in the presence of a test compound, the growth of a sample of cells which have been engineered to express a afACCase gene; (b) comparing the growth measured in step (a) to the growth of a sample of the cells in the absence of the test compound; and (c) selecting the test compound as being useful for treating a fungal infection when the growth of the sample of cells in the presence of the test compound is slower than the growth of a sample of cells in the absence of the test compound, wherein the afACCase gene has the sequence of SEQ ID NO: 1. Typically, the cell sample contains fungal cells (e.g., A. fumigatus).

The invention also includes a method for identifying an antifungal agent where the method entails: (a) contacting an ACCase polypeptide with a test compound; (b) detecting binding of the test compound to the polypeptide; and (c) determining whether a test compound that binds to the polypeptide inhibits growth of A. fumigatus, relative to growth of fungi cultured in the absence of the test compound, as an indication that the test compound is an antifungal agent. If desired, the test compound can be immobilized on a substrate, and binding of the test compound to afACCase is detected as immobilization of afAC-Case on the immobilized test compound. Immobilization of afACCase on the test compound can be detected in an immunoassay with an antibody that specifically binds to afACCase.

In still another method, binding of a test compound to an ACCase polypeptide can be detected in a conventional two-hybrid system for detecting protein/protein interactions (e.g., in yeast or mammalian cells). A test compound found to bind to afACCase can be further tested for antifungal activity in a conventional susceptibility assay. Generally, in such two-hybrid methods, (a) afACCase is provided as a fusion protein that includes the polypeptide fused to (i) a transcription activation domain of a transcription factor or (ii) a DNA-binding domain of a transcription factor; (b) the test polypeptide is provided as a fusion protein that includes the test polypeptide fused to (i) a transcription activation domain of a transcription factor or (ii) a DNA-binding domain of a transcription factor; and (c) binding of the test polypeptide to the polypeptide is detected as reconstitution of a transcription factor. Reconstitution of the transcription factor can be detected, for example, by detecting transcription of a gene that is operably linked to a DNA sequence bound by the DNA-binding domain of the reconstituted transcription factor (See, for example, White, 1996, Proc. Natl. Acad. Sci. 93:10001–10003 and references cited therein and Vidal et al., 1996, Proc. Natl. Acad. Sci. 93:10315–10320).

In an alternative method, an isolated nucleic acid molecule encoding an ACCase is used to identify a compound that decreases the expression of ACCase in vivo (i.e., in an A. fumigatus cell). Such compounds can be used as antifungal agents. To discover such compounds, cells that express an ACCase are cultured, exposed to a test compound (or a mixture of test compounds), and the level of ACCase expression or activity is compared with the level of ACCase expression or activity in cells that are otherwise identical but that have not been exposed to the test compound(s). Standard quantitative assays of gene expression and ACCase activity can be utilized in this aspect of the invention.

To identify compounds that modulate expression of ACCase the test compound(s) can be added at varying concentrations to the culture medium of A. fumigatus. Such test compounds can include small molecules (typically, non-protein, non-polysaccharide chemical entities), polypeptides, and nucleic acids. The expression of ACCase is then measured, for example, by Northern blot PCR analysis or RNAse protection analyses using a nucleic acid molecule of the invention as a probe. The level of expression in the presence of the test molecule, compared with the level of expression in its absence, will indicate whether or not the test molecule alters the expression of afACCase. Because ACCase is essential for survival, test compounds that inhibit the expression and/or function of ACCase will inhibit growth of, or kill, the cells that express ACCase.

More generally, binding of a test compound to an ACCase polypeptide can be detected either in vitro or in vivo. If desired, the above-described methods for identifying compounds that modulate the expression of the ACCase polypeptides of the invention can be combined with measuring the levels of ACCase expressed in cells, e.g., by carrying out an assay of ACCase activity, as described above or, for example, performing a Western blot analysis using antibodies that bind to ACCase. The antifungal agents identified by the methods of the invention can be used to inhibit a wide spectrum of pathogenic or non-pathogenic fungal strains.

The invention also features a method for identifying an antifungal agent, where the method entails (a) contacting an afACCase polypeptide with a test compound; (b) detecting a decrease in activity of afACCase the contacted with test compound; (c) selecting a compound useful for treating a fungal infection as one that decreases the activity of afAC-Case; and, optionally, (d) determining whether a test compound that decreases activity of a contacted afACCase polypeptide inhibits growth of fungi, relative to growth of fungi cultured in the absence of a test compound that decreases activity of a contacted ACCase polypeptide, wherein inhibition of growth indicates that the test compound is an antifungal agent, and wherein afACCase is encoded by a gene having the sequence of SEQ ID NO: 1. The test compound can be, without limitation, a polypeptide, ribonucleic acid, small molecule, deoxyribonucleic acid, antisense oligonucleotide, or ribozyme.

In yet another embodiment, the invention features a method for identifying a compound useful for treating a fungal infection, wherein the method entails (a) contacting a variant, homolog, or ortholog of an ACCase polypeptide with a test compound; (b) detecting binding of the test compound to the variant, homolog, or ortholog of afACCase; and (c) selecting a compound useful for treating a fungal infection as one that binds to the variant, homolog, or ortholog of afACCase, wherein afACCase is encoded by a gene having the sequence of SEQ ID NO: 1. Optionally, the method can also include (d) determining whether a test compound that binds to the variant, homolog, or ortholog of afACCase inhibits growth of fungi, relative to growth of fungi cultured in the absence of a test compound that binds to the variant, homolog, or ortholog of afACCase, wherein inhibition of growth indicates that the test compound is an antifungal agent. The variant, homolog, or ortholog can be derived from a non-pathogenic, or pathogenic, fungus.

Some specific embodiments of the present invention relate to assay methods for the identification of antifungal agents using assays for antifungal agents which may be carried out both in whole cell preparations and in ex vivo cell-free systems. In each instance, the assay target is the ACCase nucleotide sequence—which is essential for fungal viability—and/or the ACCase polypeptide. Candidate agents which are found to inhibit the target nucleotide sequence and/or afACCase in any assay method of the present invention are thus identified as potential antifungal agents. It is expected that the assay methods of the present invention will be suitable for both small and large-scale screening of test compounds as well as in quantitative assays such as serial dilution studies wherein the target ACCase nucleotide sequence or the ACCase polypeptide are exposed to a range of candidate agent concentrations.

When the assay methods of the present invention are carried out as a whole-cell assay, the target ACCase nucleotide sequence and/or the ACCase polypeptide and the entire living fungal cell may be exposed to the candidate agent under conditions normally suitable for growth. Optimal conditions including essential nutrients, optimal temperatures and other parameters, depend upon the particular fungal strain being used and suitable conditions are well known in the art. Inhibition of expression of the target nucleotide sequence and/or the activity of afACCase may be determined in a number of ways including observing the cell culture's growth or lack thereof. Such observation may be made visually, by optical densitometric or other light absorption/scattering means or by yet other suitable means, whether manual or automated.

In the above whole-cell assay, an observed lack of cell growth may be due to inhibition of the target nucleotide sequence and/or afACCase or may be due to an entirely different effect of the candidate agent, and further evaluation may be required to establish the mechanism of action and to determine whether the candidate agent is a specific inhibitor of the target. Accordingly, and in one embodiment of the present invention, the method may be performed as a paired-cell assay in which each test compound is separately tested against two different fungal cells, the first fungal cells having a target with altered properties making it more susceptible to inhibition compared with that of the second fungal cells.

One manner of achieving differential susceptibility is by using mutant strains expressing a modified target ACCase polypeptide. A particularly useful strain is one having a temperature sensitive ("ts") mutation as a result of which the target is more prone than the wild type target to loss of functionality at high temperatures (that is, temperatures higher than optimal, but still permitting growth in wild type cells). When grown at semi-permissive temperatures, the activity of a ts mutant target may be attenuated but sufficient for growth.

Alternatively or in conjunction with the above, differential susceptibility to target inhibitors may be obtained by using a second fungal cell which has altered properties making it less susceptible to inhibition compared with that of wild type cells as for example, a fungal cell which has been genetically manipulated to cause overexpression of the target. Such overexpression can be achieved by placing into a wild type cell a plasmid carrying the nucleotide sequence for the target. The techniques for generating temperature sensitive mutants, for preparing specific plasmids and for transforming cell lines with such plasmids are well known in the art.

Alternatively or in conjunction with the above, the access of candidate agents to a cell or an organism, may be enhanced by mutating or deleting a gene or genes which encode a protein or proteins responsible for providing a permeability barrier for a cell or an organism.

The present invention also relates to a method for identifying antifungal agents utilizing fungal cell systems that are sensitive to perturbation to one or several transcriptional/translational components.

By way of example, the present invention relates to a method of constructing mutant fungal cells in which one or more of the transcriptional/translational components is present in an altered form or in a different amount compared with a corresponding wild-type cell. This method further involves examining a candidate agent for its ability to perturb transcription/translation by assessing the impact it has on the growth of the mutant and wild-type cells. Agents that perturb transcription/translation by acting on a particular component that participates in transcription/translation may cause a mutant fungal cell which has an altered form or amount of that component to grow differently from the corresponding wild-type cell, but do not affect the growth relative to the wild type cell of other mutant cells bearing alterations in other components participating in transcription/translation. This method thus provides not only a means to identify whether a candidate agent perturbs transcription/translation but also an indication of the site at which it exerts its effects. The transcriptional/translational component which is present in altered form or amount in a cell whose growth is affected by a candidate agent is likely to be the site of action of the agent.

By way of example, the present invention provides a method for identifying antifungal agents which interfere with steps in translational accuracy, such as maintaining a proper reading frame during translation and terminating translation at a stop codon. This method involves constructing mutant fungal cells in which a detectable reporter polypeptide can only be produced if the normal process of staying in one reading frame or of terminating translation at a stop codon has been disrupted. This method further involves contacting the mutant fungal cells with a candidate agent to examine whether it increases or decreases the production of the reporter polypeptide.

The present invention also provides a method of screening an agent for specific binding affinity with afACCase (or a derivative, homolog, variant or fragment thereof) or the nucleotide sequence coding for same (including a derivative, homolog, variant or fragment thereof), the method comprising the steps of: a) providing a candidate agent; b) combining afACCase (or the derivative, homolog, variant or fragment thereof) or the nucleotide sequence coding for same (or the derivative, homolog, variant or fragment thereof) with the candidate agent for a time sufficient to allow binding under suitable conditions; such binding or interaction being associated with a second component capable of providing a detectable signal in response to the binding or interaction of the ACCase polypeptide or the nucleotide sequence encoding same with the agent; and c) determining whether the agent binds to or otherwise interacts with and activates or inhibits an activity of afACCase (or the derivative, homolog, variant or fragment thereof) or the expression of the nucleotide sequence coding for same (or the derivative, homolog, variant or fragment thereof) by detecting the presence or absence of a signal generated from the binding and/or interaction of the agent with afACCase (or the derivative, homolog, variant or fragment thereof) or the nucleotide sequence coding for same (or the derivative, homolog, variant or fragment thereof).

In other embodiments, the cell system is an extract of a fungal cell that is grown under defined conditions, and the method involves measuring transcription or translation in vitro. Such defined conditions are selected so that transcription or translation of the reporter is increased or decreased by the addition of a transcription inhibitor or a translation inhibitor to the cell extract.

One such method for identifying antifungal agents relies upon a transcription-responsive gene product. This method involves constructing a fungal cell in which the production of a reporter molecule, measured as a percentage of over-all transcription, increases or decreases under conditions in which overall fungal cell transcription is reduced. Specifically, the reporter molecule is encoded by a nucleic acid transcriptionally linked to a sequence constructed and arranged to cause a relative increase or decrease in the production of the reporter molecule when overall transcription is reduced. Typically, the overall transcription is measured by the expression of a second indicator gene whose expression, when measured as a percentage of overall transcription, remains constant when the overall transcription is reduced. The method further involves contacting the fungal cell with a candidate agent, and determining whether the agent increases or decreases the production of the first reporter molecule in the fungal cell.

In one embodiment, the reporter molecule is itself the transcription-responsive gene product whose production increases or decreases when overall transcription is reduced. In another embodiment, the reporter is a different molecule whose production is linked to that of the transcription-responsive gene product. Such linkage between the reporter and the transcription-responsive gene product can be achieved in several ways. A gene sequence encoding the reporter may, for example, be fused to part or all of the gene encoding the transcription-responsive gene product and/or to part or all of the genetic elements which control the production of the gene product. Alternatively, the transcription-responsive gene product may stimulate transcription of the gene encoding the reporter, either directly or indirectly.

Alternatively, the method for identifying antifungal agents relies upon a translation-responsive gene product. This method involves constructing a fungal cell in which the production of a reporter molecule, measured as a percentage of over-all translation, increases or decreases under conditions in which overall fungal cell translation is reduced. Specifically, the reporter molecule is encoded by nucleic acid either translationally linked or transcriptionally linked to a sequence constructed and arranged to cause a relative increase or decrease in the production of the reporter molecule when overall translation is reduced. Typically, the overall translation is measured by the expression of a second indicator gene whose expression, when measured as a percentage of overall translation, remains constant when the overall translation is reduced. The method further involves contacting the fungal cell with a candidate agent, and determining whether the agent increases or decreases the production of the first reporter molecule in the fungal cell.

In one embodiment, the reporter molecule is itself the translation-responsive gene product whose production increases or decreases when overall translation is reduced. In another embodiment, the reporter is a different molecule whose production is linked to that of the translation-responsive gene product. Such linkage between the reporter and the translation-responsive gene product can be achieved in several ways. A gene sequence encoding the reporter may, for example, be fused to part or all of the gene encoding the translation-responsive gene product and/or to part or all of the genetic elements which control the production of the gene product. Alternatively, the translation-responsive gene product may stimulate translation of the gene encoding the reporter, either directly or indirectly.

Generally, a wide variety of reporters may be used, with typical reporters providing conveniently detectable signals (eg. by spectroscopy). By way of example, a reporter gene may encode an enzyme which catalyses a reaction which alters light absorption properties.

Examples of reporter molecules include but are not limited to -galactosidase, invertase, green fluorescent protein, luciferase, chloramphenicol, acetyltransferase, beta-glucuronidase, exo-glucanase and glucoamylase. Alternatively, radiolabeled or fluorescent tag-labeled nucleotides can be incorporated into nascent transcripts which are then identified when bound to oligonucleotide probes. For example, the production of the reporter molecule can be measured by the enzymatic activity of the reporter gene product, such as -galactosidase.

In another embodiment of the present invention, a selection of hybridization probes corresponding to a predetermined population of genes of the selected fungal organism may be used to specifically detect changes in gene transcription which result from exposing the selected organism or cells thereof to a candidate agent. In this embodiment, one or more cells derived from the organism is exposed to the candidate agent in vivo or ex vivo under conditions wherein the agent effects a change in gene transcription in the cell to maintain homeostasis. Thereafter, the gene transcripts, primarily mRNA, of the cell or cells are isolated by conventional means. The isolated transcripts or cDNAs complementary thereto are then contacted with an ordered matrix of hybridization probes, each probe being specific for a different one of the transcripts, under conditions wherein each of the transcripts hybridizes with a corresponding one of the probes to form hybridization pairs. The ordered matrix of probes provides, in aggregate, complements for an ensemble of genes of the organism sufficient to model the transcriptional responsiveness of the organism to a candidate agent.

The probes are generally immobilized and arrayed onto a solid substrate such as a microtiter plate. Specific hybridization may be effected, for example, by washing the hybridized matrix with excess non-specific oligonucleotides. A hybridization signal is then detected at each hybridization pair to obtain a transcription signal profile. A wide variety of hybridization signals may be used. In one embodiment, the cells are pre-labeled with radionucleotides such that the gene transcripts provide a radioactive signal that can be detected in the hybridization pairs. The transcription signal profile of the agent-treated cells is then compared with a transcription signal profile of negative control cells to obtain a specific transcription response profile to the candidate agent.

A variety of protocols for detecting and measuring the expression of afACCase, using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on afACCase polypeptides is suitable; alternatively, a competitive binding assay may be employed. These and other assays are described, among other places, in Hampton R et al. (1990, Serological Methods, A Laboratory Manual, APS Press, St Paul Minn.) and Maddox D E et al. (1983, J. Exp. Med. 15 8:121).

In an embodiment of the present invention, afACCase or a variant, homolog, fragment or derivative thereof and/or a cell line that expresses afACCase or variant, homolog, fragment or derivative thereof may be used to screen for antibodies, peptides, or other agents, such as organic or inorganic molecules, that act as modulators of afACCase activity, thereby identifying a therapeutic agent capable of modulating the activity of afACCase. For example, antibodies that specifically bind an ACCase polypeptide and are capable of neutralizing the activity of afACCase may be used to inhibit afACCase activity. Alternatively, screening of peptide libraries or organic libraries made by combinatorial chemistry with recombinantly expressed ACCase polypeptide or a variant, homolog, fragment or derivative thereof or cell lines expressing afACCase or a variant, homolog, fragment or derivative thereof may be useful for identification of therapeutic agents that function by modulating afACCase activity. Synthetic compounds, natural products, and other sources of potentially biologically active materials can be screened in a number of ways deemed to be routine to those of skill in the art. For example, nucleotide sequences encoding the N-terminal region of afACCase can be expressed in a cell line and used for screening of allosteric modulators, either agonists or antagonists, of afACCase activity.

Accordingly, the present invention provides a method for screening a plurality of agents for specific binding affinity with afACCase, or a portion, variant, homolog, fragment or derivative thereof, by providing a plurality of agents; combining afACCase or a portion, variant, homolog, fragment or derivative thereof with each of a plurality of agents for a time sufficient to allow binding under suitable conditions; and detecting binding of afACCase, or portion, variant, homolog, fragment or derivative thereof, to each of the plurality of agents, thereby identifying the agent or agents which specifically bind afACCase. In such an assay, the plurality of agents may be produced by combinatorial chemistry techniques known to those of skill in the art.

Another technique for screening provides for high throughput screening of agents having suitable binding affinity to afACCase polypeptides and is based upon the method described in detail in WO 84/03564. In summary, large numbers of different small peptide test compounds are synthesized on a solid substrate, such as plastic pins or some other surface. The peptide test agents are reacted with afACCase fragments and washed. A bound ACCase polypeptide is then detected—such as by appropriately adapting methods well known in the art. A purified ACCase polypeptide can also be coated directly onto plates for use in the aforementioned drug screening techniques. Alternatively, non-neutralizing antibodies can be used to capture the peptide and immobilize it on a solid support.

Typically, in an antifungal discovery process, potential new antifungal agents are tested for their ability to inhibit the in vitro activity of the purified expression product of the present invention in a biochemical assay. Agents with inhibitory activity can then progress to an in vitro antifungal activity screening using a standard MIC (Minimum Inhibitory Concentration) test (based on the M27-A NCCLS approved method). Antifungal active agents identified at this point are then tested for antifungal efficacy in vivo, such as by using rodent systemic candidiasis/aspergillosis models. Efficacy is measured by measuring the agent's ability to increase the host animal's survival rate against systemic infection, and/or reduce the fungal burden in infected tissues, compared to control animals receiving no administered agent (which can be by oral or intravenous routes).

The present invention also provides a pharmaceutical composition for treating an individual in need of such treatment of a disease caused by afACCase activity (or that can be treated by inhibiting afACCase activity); the treatment method entails administering a therapeutically effective amount of an agent that affects (such as inhibits) the activity and a pharmaceutically acceptable carrier, diluent, excipient or adjuvant.

The pharmaceutical compositions can be used for humans or animals and will typically include any one or more of a pharmaceutically acceptable diluent, carrier, excipient or adjuvant. The choice of pharmaceutical carrier, excipient or diluent can be selected with regard to the intended route of administration and standard pharmaceutical practice. The pharmaceutical compositions can include as (or in addition to) the carrier, excipient, or diluent any suitable binder(s), lubricant(s), suspending agent(s), coating agent(s), solubilizing agent(s).

The invention includes pharmaceutical formulations that include a pharmaceutically acceptable excipient and an antifungal agent identified using the methods described herein. In particular, the invention includes pharmaceutical formulations that contain antifungal agents that inhibit the growth of, or kill, pathogenic fungal strains (e.g., pathogenic *Aspergillus fumigatus* strains). Such pharmaceutical formulations can be used in a method of treating a fungal infection in an organism. Such a method entails administering to the organism a therapeutically effective amount of the pharmaceutical formulation, i.e., an amount sufficient to ameliorate signs and/or symptoms of the fungal infection. In particular, such pharmaceutical formulations can be used to treat fungal infections in mammals such as humans and domesticated mammals (e.g., cows, pigs, dogs, and cats), and in plants. The efficacy of such antifungal agents in humans can be estimated in an animal model system well known to those of skill in the art (e.g., mouse systems of fungal infections).

The invention also includes (i) a method of treating a mycosal and/or fungal infection in a target (which target can be a living organism, such as a mammal, such as a human, or an inanimate target, such as a textile piece, paper, plastic etc.), which method entails delivering (such as administering or exposing) an effective amount of an agent capable of modulating the expression pattern of the nucleotide sequence of the present invention or the activity of the expression product thereof; and (ii) a method of treating a mycosal and/or fungal infection in a target (which target can be a living organism, such as a plant or a mammal, such as a human, or an inanimate target, such as a textile piece, paper, plastic etc.), which method entails delivering (such as administering or exposing) an effective amount of an agent identified by an assay according to the present invention. As used herein, the terms "treating," "treat," or "treatment" include, inter alia, preventative (e.g., prophylactic), palliative, and curative treatment of fungal infections.

The invention also features a method for inducing an immunological response in an individual, particularly a mammal, which entails inoculating the individual with one or more of the ACCase genes or polypeptides described herein, and generally in an amount adequate to produce an antibody and/or T cell immune response to protect the individual from mycoses, fungal infection, or infestations. In another aspect, the present invention relates to a method of inducing an immunological response in an individual which entails delivering to the individual a vector that includes an ACCase gene described herein or a variant, homolog, fragment, or derivative thereof in vivo to induce an immunological response, such as to produce antibody and/or a T-cell immune response to protect the individual from disease whether that disease is already established within the individual or not.

Various affinity reagents that are permeable to the microbial membrane (i.e., antibodies and antibody fragments) are useful in practicing the methods of the invention. For example polyclonal and monoclonal antibodies that specifically bind to the *A. fumigatus* ACCase polypeptide can facilitate detection of *A. fumigatus* ACCase in various fungal strains (or extracts thereof). These antibodies also are useful for detecting binding of a test compound to ACCase (e.g., using the assays described herein). In addition, monoclonal antibodies that specifically bind to *A. fumigatus* ACCase can themselves be used as antifungal agents.

In another aspect, the invention features a method for detecting an *A. fumigatus* ACCase polypeptide in a sample. This method includes: obtaining a sample suspected of containing an *A. fumigatus* ACCase polypeptide; contacting the sample with an antibody that specifically binds to an *A. fumigatus* ACCase polypeptide under conditions that allow the formation of complexes of the antibody and the ACCase polypeptide; and detecting the complexes, if any, as an indication of the presence of an *A. fumigatus* ACCase polypeptide in the sample.

In all of the foregoing methods, homologs, orthologs, or variants of the ACCase genes and polypeptides described herein can be substituted. While "homologs" are structurally similar genes contained within a species, "orthologs" are functionally equivalent genes from other species (within or outside of a given genus, e.g., from *E. coli*). The terms "variant," "homolog," or "fragment" in relation to the amino acid sequence of the ACCase of the invention include any substitution, variation, modification, replacement, deletion, or addition of one or more amino acids from or to the sequence providing the resultant ACCase polypeptide.

The invention offers several advantages. The invention provides targets, based on essential functions, for identifying potential agents for the effective treatment of opportunistic infections caused by *A. fumigatus* and other related fungal species. Also, the methods for identifying antifungal agents can be configured for high throughput screening of numerous candidate antifungal agents. Because the ACCase gene disclosed herein is thought to be highly conserved, antifungal drugs targeted to this gene or its gene products are expected to have a broad spectrum of antifungal activity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein. All publications, patent applications, patents, and other references mentioned herein are incorporated herein by reference in their entirety. In the case of a conflict, the present specification, including definitions, will control. In addition, the materials, methods, and examples are illustrative and are not intended to limit the scope of the invention, which is defined by the claims.

Other features and advantages of the invention will be apparent from the following detailed description, and from the claims.

BRIEF DESCRIPTION OF THE DRAWING

FIGS. 1A–C represent a listing of the nucleotide sequence (SEQ ID NO:1) of *Aspergillus fumigatus* (afACCase).

FIG. 2 is a listing of the predicted amino acid sequence (SEQ ID NO:2) of *Aspergillus fumigatus* (afACCase).

DETAILED DESCRIPTION OF THE INVENTION

A gene encoding acetyl coenzyme A carboxylase of *Aspergillus fumigatus* has been identified and is essential for the survival of *A. fumigatus*. The ACCase gene and polypeptide are useful targets for identifying compounds that are inhibitors of the fungi in which ACCase polypeptides are expressed.

Nucleic acids described herein include both RNA and DNA, including genomic DNA and synthetic (e.g., chemically synthesized) DNA. Nucleic acids can be double-stranded or single-stranded. Where single-stranded, the nucleic acid can be a sense strand or an antisense strand. Nucleic acids can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

An isolated nucleic acid is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a genomic DNA fragment produced by PCR or restriction endonuclease treatment) independent of other sequences. It also includes a recombinant DNA that is part of a hybrid gene encoding an additional polypeptide sequence. The terms "isolated" and "purified" refer to a nucleic acid or polypeptide that is substantially free of cellular or viral material with which it is naturally associated, or culture medium (when produced by recombinant DNA techniques), or chemical precursors or other chemicals (when chemically synthesized). Moreover, an isolated nucleic acid fragment is a nucleic acid fragment that is not naturally occurring as a fragment and would not be found in the natural state.

A nucleic acid sequence that is substantially identical to an ACCase nucleotide sequence is at least 80% identical to the nucleotide sequence of ACCase as represented by the SEQ ID NO:1, as depicted in FIGS. 1A–C. For purposes of comparison of nucleic acids, the length of the reference nucleic acid sequence will generally be at least 40 nucleotides, e.g., at least 60 nucleotides or more nucleotides.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of overlapping positions×100). Preferably, the two sequences are the same length.

The determination of percent identity or homology between two sequences can be accomplished using a mathematical algorithm. A preferred, non-limiting example of a mathematical algorithm utilized for the comparison of two sequences is the algorithm of Karlin and Altschul (1990) *Proc. Nat'l Acad. Sci. USA* 87:2264–2268, modified as in Karlin and Altschul (1993) *Proc. Nat'l Acad. Sci. USA* 90:5873–5877. Such an algorithm is incorporated into the NBLAST and XBLAST programs of Altschul, et al. (1990); *J. Mol. Biol.* 215:403–410. BLAST nucleotide searches can be performed with the NBLAST program, score=100, wordlength=12 to obtain nucleotide sequences homologous to ACCase nucleic acid molecules of the invention. BLAST protein searches can be performed with the XBLAST program, score=50, wordlength=3 to obtain amino acid sequences homologous to ACCase protein molecules of the invention. To obtain gapped alignments for comparison purposes, Gapped BLAST can be utilized as described in Altschul et al., (1997) *Nucleic Acids Res.* 25:3389–3402. When utilizing BLAST and Gapped BLAST programs, the default parameters of the respective programs (e.g., XBLAST and NBLAST) can be used. See the web site at the National Center for Biotechnology Information (ncbi.nlm.hih.gov.). Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

The terms "variant," "homolog," or "fragment" in relation to the nucleotide sequence encoding afACCase of the present invention include any substitution, variation, modification, replacement, deletion, or addition of one (or more) nucleotides from or to the sequence of an ACCase gene. Typically, the resultant nucleotide sequence encodes or is capable of encoding an ACCase polypeptide that generally is at least as biologically active as the referenced ACCase polypeptide (e.g., as represented by SEQ ID NO:2). In particular, the term "homolog" covers homology with respect to structure and/or function providing the resultant nucleotide sequence codes for or is capable of coding for an ACCase polypeptide being at least as biologically active as afACCase encoded by the sequence shown as SEQ ID NO:1. With respect to sequence homology, there is at least 75% (e.g., 85%, 90%, 95%, 98%, or 100%) homology to the sequence shown as SEQ ID NO:1. The term "homology" as used herein can be equated with the term "identity". Relative sequence homology (i.e., sequence identity) can be determined by commercially available computer programs that can calculate the percent homology between two or more sequences. A typical example of such a computer program is CLUSTAL.

"Substantial homology," where homology indicates sequence identity, means at least 80% sequence identity, as judged by direct sequence alignment and comparison. "Substantial homology" when assessed by the BLAST algorithm equates to sequences which match with an EXPECT value of at least about 7, e.g., at least about 9, 10, or more. The default threshold for EXPECT in BLAST searching is usually 10.

Also included within the scope of the present invention are alleles of afACCase gene. As used herein, an "allele" or "allelic sequence" is an alternative form of afACCase. Alleles result from a mutation, i.e., a change in the nucleotide sequence, and generally produce altered mRNAs or polypeptides whose structure or function may or may not be altered. Any given gene can have none, one, or more than one allelic form. Common mutational changes which give rise to alleles are generally ascribed to deletions, additions or substitutions of amino acids. Each of these types of changes can occur alone, or in combination with the others, one or more times in a given sequence.

The ACCase polypeptides of the invention include, but are not limited to, recombinant polypeptides and natural polypeptides. Also included are nucleic acid sequences that encode forms of ACCase polypeptides in which naturally occurring amino acid sequences are altered or deleted. Preferred nucleic acids encode polypeptides that are soluble under normal physiological conditions. Also within the invention are nucleic acids encoding fusion proteins in which a portion of the ACCase polypeptide is fused to an unrelated polypeptide (e.g., a marker polypeptide or a fusion partner) to create a fusion protein. For example, the polypeptide can be fused to a hexa-histidine tag to facilitate purification of bacterially expressed polypeptides, or to a hemagglutinin tag to facilitate purification of polypeptides expressed in eukaryotic cells. The invention also includes, for example, isolated polypeptides (and the nucleic acids that encode these polypeptides) that include a first portion and a second portion; the first portion includes, e.g., an ACCase polypeptide, and the second portion includes an immunoglobulin constant (Fc) region or a detectable marker.

The fusion partner can be, for example, a polypeptide that facilitates secretion, e.g., a secretory sequence. Such a fused polypeptide is typically referred to as a preprotein. The secretory sequence can be cleaved by the host cell to form the mature protein. Also within the invention are nucleic acids that encode an ACCase polypeptide fused to a polypeptide sequence to produce an inactive preprotein. Preproteins can be converted into the active form of the protein by removal of the inactivating sequence.

The invention also includes nucleic acids that hybridize, e.g., under stringent hybridization conditions (as defined herein) to all or a portion of the nucleotide sequences represented by SEQ ID NO:1, or its complement. The hybridizing portion of the hybridizing nucleic acids is typically at least 15 (e.g., 20, 30, or 50) nucleotides in length. The hybridizing portion of the hybridizing nucleic acid is at least 60%, e.g., at least 70%, 80%, 95%, or at least 98% or 100%, identical to the sequence of a portion or all of a nucleic acid encoding an ACCase polypeptide or its complement. Hybridizing nucleic acids of the type described herein can be used as a cloning probe, a primer (e.g., a PCR primer), or a diagnostic probe. Nucleic acids that hybridize to the nucleotide sequence represented by SEQ ID NO: 1 are considered "antisense oligonucleotides."

Also useful in the invention are various engineered cells, e.g., transformed host cells, that contain an ACCase nucleic acid described herein. A transformed cell is a cell into which (or into an ancestor of which) has been introduced, by means of recombinant DNA techniques, a nucleic acid encoding an ACCase polypeptide. Both prokaryotic and eukaryotic cells are included, e.g., fungi, and bacteria, such as *E. coli*, and the like.

Also useful in the invention are genetic constructs (e.g., vectors and plasmids) that include a nucleic acid of the invention operably linked to a transcription and/or translation sequence to enable expression, e.g., expression vectors. A selected nucleic acid, e.g., a DNA molecule encoding an ACCase polypeptide, is "operably linked" when it is positioned adjacent to one or more sequence elements, e.g., a promoter, which direct transcription and/or translation of the sequence such that the sequence elements can control transcription and/or translation of the selected nucleic acid.

The invention also features purified or isolated polypeptides encoded by the *A. fumigatus* ACCase coding sequence. The terms "protein" and "polypeptide" both refer to any chain of amino acids, regardless of length or post-translational modification (e.g., glycosylation or phosphorylation). Thus, the term ACCase polypeptide includes full-length, naturally occurring, isolated ACCase proteins, as well as recombinantly or synthetically produced polypeptides that correspond to the full-length, naturally occurring proteins, or to a portion of the naturally occurring or synthetic polypeptide.

A purified or isolated compound is a composition that is at least 60% by weight the compound of interest, e.g., an ACCase polypeptide or antibody. Preferably the preparation is at least 75% (e.g., at least 90%, 95%, or even 99%) by weight the compound of interest. Purity can be measured by any appropriate standard method, e.g., column chromatography, polyacrylamide gel electrophoresis, or HPLC analysis.

Preferred ACCase polypeptides include a sequence substantially identical to all or a portion of a naturally occurring *A. fumigatus* ACCase polypeptide, e.g., including all or a portion of the sequences shown in FIG. 2. Polypeptides "substantially identical" to the ACCase polypeptide sequences described herein have an amino acid sequence that is at least 65% identical to the amino acid sequence of the ACCase polypeptide represented by the SEQ ID NO:2 (measured as described herein). The new polypeptides can also have a greater percentage identity, e.g., 85%, 90%, 95%, or even higher. For purposes of comparison, the length of the reference ACCase polypeptide sequence will generally be at least 16 amino acids, e.g., at least 20 or 25 amino acids.

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference polypeptide. Thus, a polypeptide that is 50% identical to a reference polypeptide that is 100 amino acids long can be a 50 amino acid polypeptide that is completely identical to a 50 amino acid long portion of the reference polypeptide. It also might be a 100 amino acid long polypeptide which is 50% identical to the reference polypeptide over its entire length. Of course, other polypeptides also will meet the same criteria.

The invention also features purified or isolated antibodies that specifically bind to an *A. fumigatus* ACCase polypeptide. An antibody "specifically binds" to a particular antigen, e.g., an ACCase polypeptide, when it binds to that antigen, but does not recognize and bind to other molecules in a sample, e.g., a biological sample, that naturally includes an ACCase polypeptide. In addition, an antibody specifically binds to an *A. fumigatus* ACCase polypeptide when it does not substantially bind to ACCase polypeptides from other genuses (e.g., Saccharomyces), particularly ACCase polypeptides of an organism to be treated by the methods of the invention (e.g., humans, or domesticated animals).

Identifying the *Aspergillus fumigatus* ACCase Gene

As shown by the experiments described below, the *Aspergillus fumigatus* ACCase gene is essential for survival. *Aspergillus fumigatus* is available from the ATCC. The *A. fumigatus* ACCase gene was cloned using polymerase chain reaction technology and degenerate primers based on the *Saccharomyces cerevisiae* ACCase gene. The degenerate primers were used to amplify genomic *Aspergillus fumigatus* DNA using 35 cycles of: 94° C. for 1 minute, 40° C. for 2 minutes, and 72° C. for 3 minutes. The resulting PCR product was subcloned into the pBluescript cloning vector (Stratagene; La Jolla, Calif.), then sequenced. Based on the resulting sequence, two exact-match primers were created, and the exact-match primers were used to PCR amplify the 5' and 3' halves of the afACCase from an *Aspergillus fumigatus* cDNA library. The cDNA library was made using the vector pYES2 (Invitrogen; Palo Alto, Calif.). For PCR amplification, one exact-match primer was paired with a primer hybridizing to the 3' sequence of the multiple cloning site of pYES2. The other exact-match primer was paired with a primer hybridizing to the pGAL sequences in pYES2. PCR amplification of the 5' and 3' halves of the ACCase gene was carried out with 30 cycles of 94° C. for 30 seconds, 55° C. for 30 seconds, 72° for and 2.5 minutes. The resulting PCR products were cloned into the pBluescript vector and sequenced to obtain the cDNA sequence of *Aspergillus fumigatus* ACCase. The entire ACCase open reading frame was subsequently amplified using primers that exactly matched each of (a) the first methionine codon and (b) the stop codon of the ACCase open reading frame. The amplified open reading frame subsequently was cloned into the pCRTOPO vector (Invitrogen) using TA cloning methods (Invitrogen).

Identification of ACCase Genes in Additional Fungal Strains

Since the *Aspergillus fumigatus* ACCase gene has been identified, this gene, or fragments thereof, can be used to detect homologous genes in yet other organisms. Fragments of a nucleic acid (DNA or RNA) encoding an ACCase polypeptide (or sequences complementary thereto) can be used as probes in conventional nucleic acid hybridization assays of various organisms. For example, nucleic acid probes (which typically are 8–30, or usually 15–20, nucleotides in length) can be used to detect ACCase genes in art-known molecular biology methods, such as Southern blotting, Northern blotting, dot or slot blotting, PCR amplification methods, colony hybridization methods, and the like. Typically, an oligonucleotide probe based on the nucleic acid sequences described herein, or fragment thereof, is labeled and used to screen a genomic library constructed from mRNA obtained from a fungal strain of interest. A suitable method of labeling involves using polynucleotide kinase to add $^{32}$P-labeled ATP to the oligonucleotide used as the probe. This method is well known in the art, as are several other suitable methods (e.g., biotinylation and enzyme labeling).

Hybridization of the oligonucleotide probe to the library, or other nucleic acid sample, typically is performed under moderate to high stringency conditions. Nucleic acid duplex or hybrid stability is expressed as the melting temperature or $T_m$, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE). Then, assuming that 1% mismatching results in a 1° C. decrease in the $T_m$, the temperature of the final wash in the hybridization reaction is reduced accordingly (for example, if sequences having ≧95% identity with the probe are sought, the final wash temperature is decreased by 5° C.). In practice, the change in $T_m$ can be between 0.5° and 1.5° C. per 1% mismatch.

High stringency conditions are hybridizing at 68° C. in 5×SSC/5×Denhardt's solution/1.0% SDS, or in 0.5 M NaHPO$_4$ (pH 7.2)/1 mM EDTA/7% SDS, or in 50% formamide/0.25 M NaHPO$_4$ (pH 7.2)/0.25 M NaCl/1 mM EDTA/7% SDS; and washing in 0.2×SSC/0.1% SDS at room temperature or at 42° C., or in 0.1×SSC/0.1% SDS at 68° C., or in 40 mM NaHPO$_4$ (pH 7.2)/1 mM EDTA/5% SDS at 50° C., or in 40 mM NaHPO$_4$ (pH 7.2) 1 mM EDTA/1% SDS at 50° C. Stringent conditions include washing in 3×SSC at 42° C. The parameters of salt concentration and temperature can be varied to achieve the optimal level of identity between the probe and the target nucleic acid. Additional guidance regarding such conditions is available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

In one approach, libraries constructed from pathogenic or non-pathogenic fungal strains are screened. For example, such strains can be screened for expression of the ACCase gene of the invention by Northern blot analysis. Upon detection of transcripts of the ACCase gene, libraries can be constructed from RNA isolated from the appropriate strain, utilizing standard techniques well known to those of skill in the art. Alternatively, a total genomic DNA library can be screened using an ACCase gene probe.

New gene sequences can be isolated, for example, by performing PCR using two degenerate oligonucleotide primer pools designed on the basis of nucleotide sequences within the ACCase gene as depicted herein. The template for the reaction can be DNA obtained from strains known or suspected to express the ACCase gene of the invention. The PCR product can be subcloned and sequenced.

Synthesis of the various ACCase polypeptides (or an antigenic fragment thereof) for use as antigens, or for other purposes, can be accomplished using any of the various art-known techniques. For example, an ACCase polypeptide, or an antigenic fragment(s), can be synthesized chemically in vitro, or enzymatically (e.g., by in vitro transcription and translation). Alternatively, the gene can be expressed in, and the polypeptide purified from, a cell (e.g., a cultured cell) by using any of the numerous, available gene expression systems. For example, the polypeptide antigen can be produced in a prokaryotic host (e.g., *E. coli*) or in eukaryotic cells, such as yeast cells.

Proteins and polypeptides can also be produced in plant cells, if desired. For plant cells, viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Rockland, Md.; also, see, e.g., Ausubel et al., *Current Protocols in Molecular Biology*, John Wiley & Sons, New York, 1994). The optimal methods of transformation or transfection and the choice of expression vehicle will depend on the host system selected. Transformation and transfection methods are described, e.g., in Ausubel et al., supra; expression vehicles can be chosen from those provided, e.g., in *Cloning Vectors: A Laboratory Manual* (P. H. Pouwels et al., 1985, Supp. 1987). The host cells harboring the expression vehicle can be cultured in conventional nutrient media, adapted as needed for activation of a chosen gene, repression of a chosen gene, selection of transformants, or amplification of a chosen gene.

If desired, ACCase polypeptide can be produced as a fusion protein. For example, the expression vector pUR278 (Ruther et al., *EMBO J.*, 2:1791, 1983) can be used to create lacZ fusion proteins. The art-known pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an exemplary expression system, a baculovirus such as *Autographa californica* nuclear polyhedrosis virus (AcNPV), which grows in *Spodoptera frugiperda* cells, can be used as a vector to express foreign genes. A coding sequence encoding an ACCase polypeptide can be cloned into a non-essential region (for example the polyhedrin gene) of the viral genome and placed under control of a promoter, e.g., the polyhedrin promoter or an exogenous promoter. Successful insertion of a gene encoding an ACCase polypeptide can result in inactivation of the polyhedrin gene and production of non-occluded recombinant virus (i.e., virus lacking the proteinaceous coat encoded by the polyhedrin gene). These recombinant viruses are then typically used to infect insect cells (e.g., *Spodoptera frugiperda* cells) in which the inserted gene is expressed (see, e.g., Smith et al., *J. Virol.*, 46:584, 1983; Smith, U.S. Pat. No. 4,215,051). If desired, mammalian cells can be used in lieu of insect cells, provided that the virus is engineered such that the gene encoding the ACCase polypeptide is placed under the control of a promoter that is active in mammalian cells.

In mammalian host cells, a number of viral-based expression systems can be utilized. When an adenovirus is used as an expression vector, the nucleic acid sequence encoding the ACCase polypeptide can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) will result in a recombinant virus that is viable and capable of expressing an ACCase gene product in infected hosts (see, e.g., Logan, Proc. Natl. Acad. Sci. USA, 81:3655, 1984).

Specific initiation signals can be required for efficient translation of inserted nucleic acid sequences. These signals include the ATG initiation codon and adjacent sequences. In general, exogenous translational control signals, including, perhaps, the ATG initiation codon, should be provided. Furthermore, the initiation codon must be in phase with the reading frame of the desired coding sequence to ensure translation of the entire sequence. These exogenous translational control signals and initiation codons can be of a variety of origins, both natural and synthetic. The efficiency of expression can be enhanced by the inclusion of appropriate transcription enhancer elements, or transcription terminators (Bittner et al., *Methods in Enzymol.*, 153:516, 1987).

The ACCase polypeptide can be expressed individually or as a fusion with a heterologous polypeptide, such as a signal sequence or other polypeptide having a specific cleavage site at the N- and/or C-terminus of the protein or polypeptide. The heterologous signal sequence selected should be one that is recognized and processed, i.e., cleaved by a signal peptidase, by the host cell in which the fusion protein is expressed.

A host cell can be chosen that modulates the expression of the inserted sequences, or modifies and processes the gene product in a specific, desired fashion. Such modifications and processing (e.g., cleavage) of protein products can facilitate optimal functioning of the protein. Various host cells have characteristic and specific mechanisms for post-translational processing and modification of proteins and gene products. Appropriate cell lines or host systems familiar to those of skill in the art of molecular biology can be chosen to ensure the correct modification and processing of the foreign protein expressed. To this end, eukaryotic host cells that possess the cellular machinery for proper processing of the primary transcript, and phosphorylation of the gene product can be used. Such mammalian host cells include, but are not limited to, CHO, VERO, BHK, HeLa, COS, MDCK, 293, 3T3, WI38, and choroid plexus cell lines.

If desired, the ACCase polypeptide can be produced by a stably-transfected mammalian cell line. A number of vectors suitable for stable transection of mammalian cells are available to the public, see, e.g., Pouwels et al. (supra); methods for constructing such cell lines are also publicly known, e.g., in Ausubel et al. (supra). In one example, DNA encoding the protein is cloned into an expression vector that includes the dihydrofolate reductase (DHFR) gene. Integration of the plasmid and, therefore, the gene encoding the afACCase polypeptide into the host cell chromosome is selected for by including 0.01–300 $\mu$M methotrexate in the cell culture medium (as described in Ausubel et al., supra). This dominant selection can be accomplished in most cell types.

Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra).

A number of other selection systems can be used, including but not limited to, herpes simplex virus thymidine kinase genes, hypoxanthine-guanine phosphoribosyl-transferase genes, and adenine phosphoribosyltransferase genes, which can be employed in tk, hgprt, or aprt cells, respectively. In addition, gpt, which confers resistance to mycophenolic acid (Mulligan et al., *Proc. Natl. Acad. Sci. USA*, 78:2072, 1981); neo, which confers resistance to the aminoglycoside G-418 (Colberre-Garapin et al., *J. Mol. Biol.*, 150:1, 1981); and hygro, which confers resistance to hygromycin (Santerre et al., *Gene*, 30:147, 1981), can be used.

Alternatively, any fusion protein can be purified by utilizing an antibody or other molecule that specifically bind to the fusion protein being expressed. For example, a system described in Janknecht et al., *Proc. Natl. Acad. Sci. USA*, 88:8972 (1981), allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns, and histidine-tagged proteins are selectively eluted with imidazole-containing buffers.

Alternatively, an ACCase polypeptide, or a portion thereof, can be fused to an immunoglobulin Fc domain. Such a fusion protein can be purified using a protein A column, for example. Moreover, such fusion proteins permit the production of a chimeric form of an ACCase polypeptide having increased stability in vivo.

Once the recombinant ACCase polypeptide is expressed, it can be isolated (i.e., purified). Secreted forms of the polypeptides can be isolated from cell culture media, while non-secreted forms must be isolated from the host cells. Polypeptides can be isolated by affinity chromatography. For example, an anti-ACCase antibody (e.g., produced as described herein) can be attached to a column and used to isolate the protein. Lysis and fractionation of cells harboring the protein prior to affinity chromatography can be performed by standard methods (see, e.g., Ausubel et al., supra). Alternatively, a fusion protein can be constructed and used to isolate an ACCase polypeptide (e.g., an ACCase-maltose binding fusion protein, an ACCase-galactosidase fusion protein, or an ACCase-trpE fusion protein; see, e.g., Ausubel et al., supra; New England Biolabs Catalog, Beverly, Mass.). The recombinant protein can, if desired, be further purified, e.g., by high performance liquid chromatography using standard techniques (see, e.g., Fisher, *Laboratory Techniques In Biochemistry And Molecular Biology*, eds., Work and Burdon, Elsevier, 1980).

Given the amino acid sequences described herein, polypeptides useful in practicing the invention, particularly fragments of afACCase, can be produced by standard chemical synthesis (e.g., by the methods described in Solid Phase Peptide Synthesis, 2nd ed., The Pierce Chemical Co., Rockford, Ill., 1984) and used as antigens, for example.

Antibodies

The ACCase polypeptides (or antigenic fragments or analogs of such polypeptides) can be used to raise antibodies useful in the invention, and such polypeptides can be produced by recombinant or peptide synthetic techniques (see, e.g., Solid Phase Peptide Synthesis, supra; Ausubel et al., supra). In general, the polypeptides can be coupled to a carrier protein, such as KLH, as described in Ausubel et al., supra, mixed with an adjuvant, and injected into a host mammal. A "carrier" is a substance that confers stability on, and/or aids or enhances the transport or immunogenicity of, an associated molecule. Antibodies can be purified, for example, by affinity chromatography methods in which the polypeptide antigen is immobilized on a resin.

In particular, various host animals can be immunized by injection of a polypeptide of interest. Examples of suitable host animals include rabbits, mice, guinea pigs, and rats. Various adjuvants can be used to increase the immunological response, depending on the host species, including but not limited to Freund's (complete and incomplete adjuvant), adjuvant mineral gels such as aluminum hydroxide, surface active substances such as lysolecithin, pluronic polyols, polyanions, peptides, oil emulsions, keyhole limpet hemocyanin, dinitrophenol, BCG (bacille Calmette-Guerin) and *Corynebacterium parvum*. Polyclonal antibodies are heterogeneous populations of antibody molecules derived from the sera of the immunized animals.

Antibodies useful in the invention include monoclonal antibodies, polyclonal antibodies, humanized or chimeric antibodies, single chain antibodies, Fab fragments, $F(ab')_2$ fragments, and molecules produced using a Fab expression library.

Monoclonal antibodies (mAbs), which are homogeneous populations of antibodies to a particular antigen, can be prepared using ACCase, and standard hybridoma technology (see, e.g., Kohler et al., *Nature*, 256:495, 1975; Kohler et al., *Eur. J. Immunol.*, 6:511, 1976; Kohler et al., *Eur. J. Immunol.*, 6:292, 1976; Hammerling et al., In *Monoclonal Antibodies and T Cell Hybridomas*, Elsevier, NY, 1981; Ausubel et al., supra).

In particular, monoclonal antibodies can be obtained by any technique that provides for the production of antibody molecules by continuous cell lines in culture, such as those described in Kohler et al., *Nature*, 256:495, 1975, and U.S. Pat. No. 4,376,110; the human B-cell hybridoma technique (Kosbor et al., *Immunology Today*, 4:72, 1983; Cole et al., *Proc. Natl. Acad. Sci. USA*, 80:2026, 1983); and the EBV-hybridoma technique (Cole et al., *Monoclonal Antibodies and Cancer Therapy*, Alan R. Liss, Inc., pp. 77–96, 1983). Such antibodies can be of any immunoglobulin class including IgG, IgM, IgE, IgA, IgD, and any subclass thereof. The hybridomas producing the mAbs of this invention can be cultivated in vitro or in vivo.

Once produced, polyclonal or monoclonal antibodies are tested for specific recognition of *A. fumigatus* ACCase in an immunoassay, such as a Western blot or immunoprecipitation analysis using standard techniques, e.g., as described in Ausubel et al., supra. Antibodies that specifically bind to the ACCase polypeptide, or conservative variants are useful in the invention. For example, such antibodies can be used in an immunoassay to detect an ACCase polypeptide in pathogenic or non-pathogenic strains of fungi.

Preferably, antibodies of the invention are produced using fragments of ACCase that appear likely to be antigenic, by criteria such as high frequency of charged residues. In one specific example, such fragments are generated by standard techniques of PCR, and are then cloned into the pGEX expression vector (Ausubel et al., supra). Fusion proteins are expressed in *E. coli* and purified using a glutathione agarose affinity matrix as described in Ausubel, et al., supra.

If desired, several (e.g., two or three) fusions can be generated for each protein, and each fusion can be injected into at least two rabbits. Antisera can be raised by injections in a series, typically including at least three booster injections. Typically, the antisera is checked for its ability to immunoprecipitate a recombinant ACCase polypeptide, or unrelated control proteins, such as glucocorticoid receptor, chloramphenicol acetyltransferase, or luciferase.

Techniques developed for the production of "chimeric antibodies" (Morrison et al., *Proc. Natl. Acad. Sci.*, 81:6851, 1984; Neuberger et al., *Nature*, 312:604, 1984; Takeda et al., *Nature*, 314:452, 1984) can be used to splice the genes from a mouse antibody molecule of appropriate antigen specificity together with genes from a human antibody molecule of appropriate biological activity. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. Nos. 4,946,778; 4,946,778 and 4,704,692) can be adapted to produce single chain antibodies against an ACCase polypeptide. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments can include but are not limited to $F(ab')_2$ fragments, which can be produced by pepsin digestion of the antibody molecule, and Fab fragments, which can be generated by reducing the disulfide bridges of $F(ab')_2$ fragments. Alternatively, Fab expression libraries can be constructed (Huse et al., *Science*, 246:1275, 1989) to allow rapid and easy identification of monoclonal Fab fragments with the desired specificity.

Polyclonal and monoclonal antibodies that specifically bind to an ACCase polypeptide can be used, for example, to detect expression of ACCase in another strain of fungi. For example, an ACCase polypeptide can be detected in conventional immunoassays of fungal cells or extracts. Examples of suitable assays include, without limitation, Western blotting, ELISAs, radioimmune assays, and the like.

Assay for Antifungal Agents

The invention provides a method for identifying an antifungal agent(s). Although the inventor is not bound by any particular theory as to the biological mechanism involved, the new antifungal agents are thought to inhibit specifically (1) the function of the ACCase polypeptide or (2) expression of the ACCase gene. In preferred methods, screening for antifungal agents is accomplished by identifying those compounds (e.g., small organic molecules) that inhibit the activity of an ACCase polypeptide or the expression of an ACCase gene. Because ACCase is essential for the survival of *A. fumigatus*, compounds that inhibit ACCase in such assays are expected to be antifungal agents and can be further tested, if desired, in conventional susceptibility assays.

In various suitable methods, screening for antifungal agents is accomplished by (i) identifying those compounds that bind to ACCase and (ii) further testing such compounds for their ability to inhibit fungal growth in vitro or in vivo.

Specific binding of a test compound to a polypeptide can be detected, for example, in vitro by reversibly or irreversibly immobilizing the test compound(s) on a substrate, e.g., the surface of a well of a 96-well polystyrene microtiter plate. Methods for immobilizing polypeptides and other small molecules are well known in the art. For example, the microtiter plates can be coated with an ACCase polypeptide by adding the polypeptide in a solution (typically, at a concentration of 0.05 to 1 mg/ml in a volume of 1–100 µl) to each well, and incubating the plates at room temperature to 37° C. for 0.1 to 36 hours. Polypeptides that are not bound to the plate can be removed by shaking the excess solution from the plate, and then washing the plate (once or repeatedly) with water or a buffer. Typically, the polypeptide is in water or a buffer. The plate is then washed with a buffer that lacks the bound polypeptide. To block the free protein-binding sites on the plates, the plates are blocked with a protein that is unrelated to the bound polypeptide. For example, 300 µl of bovine serum albumin (BSA) at a concentration of 2 mg/ml in Tris-HCl is suitable. Suitable substrates include those substrates that contain a defined cross-linking chemistry (e.g., plastic substrates, such as polystyrene, styrene, or polypropylene substrates from Corning Costar Corp. (Cambridge, Mass.), for example). If desired, a beaded particle, e.g., beaded agarose or beaded sepharose, can be used as the substrate. ACCase is then added to the coated plate and allowed to bind to the test compound (e.g., at 37° C. for 0.5–12 hours). The plate then is rinsed as described above.

Binding of the test compound to ACCase can be detected by any of a variety of art-known methods. For example, an antibody that specifically binds to an ACCase polypeptide can be used in an immunoassay. If desired, the antibody can be labeled (e.g., fluorescently or with a radioisotope) and detected directly (see, e.g., West and McMahon, *J. Cell Biol.* 74:264, 1977). Alternatively, a second antibody can be used for detection (e.g., a labeled antibody that binds to the Fc portion of an anti-YphC antibody). In an alternative detection method, the ACCase polypeptide is labeled, and the label is detected (e.g., by labeling an ACCase polypeptide with a radioisotope, fluorophore, chromophore, or the like). In still another method, the ACCase polypeptide is produced as a fusion protein with a protein that can be detected optically, e.g., green fluorescent protein (which can be detected under UV light). In an alternative method, the polypeptide can be produced as a fusion protein with an enzyme having a detectable enzymatic activity, such as horse radish peroxidase, alkaline phosphatase, -galactosidase, or glucose oxidase. Genes encoding all of these enzymes have been cloned and are available for use by those of skill in the art. If desired, the fusion protein can include an antigen, and such an antigen can be detected and measured with a polyclonal or monoclonal antibody using conventional methods. Suitable antigens include enzymes (e.g., horse radish peroxidase, alkaline phosphatase, and -galactosidase) and non-enzymatic polypeptides (e.g., serum proteins, such as BSA and globulins, and milk proteins, such as caseins).

In various in vivo methods for identifying polypeptides that bind to ACCase, the conventional two-hybrid assays of protein/protein interactions can be used (see e.g., Chien et al., *Proc. Natl. Acad. Sci. USA,* 88:9578, 1991; Fields et al., U.S. Pat. No. 5,283,173; Fields and Song, *Nature,* 340:245, 1989; Le Douarin et al., *Nucleic Acids Research,* 23:876, 1995; Vidal et al., *Proc. Natl. Acad. Sci. USA,* 93:10315–10320, 1996; and White, *Proc. Natl. Acad. Sci. USA,* 93:10001–10003, 1996). Generally, the two-hybrid methods involve in vivo reconstitution of two separable domains of a transcription factor. One fusion protein contains the ACCase polypeptide fused to either a transactivator domain or DNA binding domain of a transcription factor (e.g., of Gal4). The other fusion protein contains a test polypeptide fused to either the DNA binding domain or a transactivator domain of a transcription factor. Once brought together in a single cell (e.g., a yeast cell or mammalian cell), one of the fusion proteins contains the transactivator domain and the other fusion protein contains the DNA binding domain. Therefore, binding of the ACCase polypeptide to the test polypeptide (i.e., candidate antifungal agent) reconstitutes the transcription factor. Reconstitution of the transcription factor can be detected by detecting expression of a gene (i.e., a reporter gene) that is operably linked to a DNA sequence that is bound by the DNA binding domain of the transcription factor. Kits for practicing various two-hybrid methods are commercially available (e.g., from Clontech; Palo Alto, Calif.).

The methods described above can be used for high throughput screening of numerous test compounds to identify candidate antifungal (or anti-fungal) agents. Having identified a test compound as a candidate antifungal agent, the candidate antifungal agent can be further tested for inhibition of fungal growth in vitro or in vivo (e.g., using an animal, e.g., rodent, model system) if desired. Using other, art-known variations of such methods, one can test the ability of a nucleic acid (e.g., DNA or RNA) used as the test compound to bind to ACCase.

In vitro, further testing can be accomplished by means known to those in the art such as an enzyme inhibition assay or a whole-cell fungal growth inhibition assay. For example, an agar dilution assay identifies a substance that inhibits fungal growth. Microtiter plates are prepared with serial dilutions of the test compound, adding to the preparation a given amount of growth substrate, and providing a preparation of fungi. Inhibition of fungal growth is determined, for example, by observing changes in optical densities of the fungal cultures.

Inhibition of fungal growth is demonstrated, for example, by comparing (in the presence and absence of a test compound) the rate of growth or the absolute growth of fungal cells. Inhibition includes a reduction in the rate of growth or absolute growth by at least 20%. Particularly potent test compounds can further reduce the growth rate (e.g., by at least 25%, 30%, 40%, 50%, 75%, 80%, or 90%).

Animal (e.g., rodent such as murine) models of fungal infections are known to those of skill in the art, and such animal model systems are accepted for screening antifungal agents as an indication of their therapeutic efficacy in human patients. In a typical in vivo assay, an animal is infected with a pathogenic strain of fungi, e.g., by inhalation of fungi, and conventional methods and criteria are used to diagnose the mammal as being afflicted with a fungal infection. The candidate antifungal agent then is administered to the mammal at a dosage of 1–100 mg/kg of body weight, and the mammal is monitored for signs of amelioration of disease. Alternatively, the test compound can be administered to the mammal prior to infecting the mammal with the fungi, and the ability of the treated mammal to resist infection is measured. Of course, the results obtained in the presence of the test compound should be compared with results in control animals, which are not treated with the test compound. Administration of candidate antifungal agents to the mammal can be carried out as described below, for example.

Pharmaceutical Formulations

Treatment includes administering a pharmaceutically effective amount of a composition containing an antifungal agent to a subject in need of such treatment, thereby inhibiting fungal growth in the subject. Such a composition typically contains from about 0.1 to 90% by weight (such as 1 to 20% or 1 to 10%) of an antifungal agent of the invention in a pharmaceutically acceptable carrier.

Solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate and alginic acid. Tablet binders that can be used include acacia, methylcellulose, sodium carboxymethylcellulose, polyvinylpyrrolidone (Povidone), hydroxypropyl methylcellulose, sucrose, starch, and ethylcellulose. Lubricants that can be used include magnesium stearates, stearic acid, silicone fluid, talc, waxes, oils, and colloidal silica.

Liquid formulations of the compositions for oral administration prepared in water or other aqueous vehicles can contain various suspending agents such as methylcellulose, alginates, tragacanth, pectin, kelgin, carrageenan, acacia, polyvinylpyrrolidone, and polyvinyl alcohol. The liquid formulations can also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

Injectable formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water soluble versions of the compounds can be administered by the drip method, whereby a pharmaceutical formulation containing the antifungal agent and a physiologically acceptable excipient is infused. Physiologically acceptable excipients can include, for example, 5% dextrose, 0.9% saline, Ringer's solution or other suitable excipients. Intramuscular preparations, a sterile formulation of a suitable soluble salt form of the compounds can be dissolved and administered in a pharmaceutical excipient such as Water-for-Injection, 0.9% saline, or 5% glucose solution. A suitable insoluble form of the compound can be prepared and administered as a suspension in an aqueous base or a pharmaceutically acceptable oil base, such as an ester of a long chain fatty acid, (e.g., ethyl oleate).

A topical semi-solid ointment formulation typically contains a concentration of the active ingredient from about 1 to 20%, e.g., 5 to 10% in a carrier such as a pharmaceutical cream base. Various formulations for topical use include drops, tinctures, lotions, creams, solutions, and ointments containing the active ingredient and various supports and vehicles.

The optimal percentage of the antifungal agent in each pharmaceutical formulation varies according to the formulation itself and the therapeutic effect desired in the specific pathologies and correlated therapeutic regimens. Appropriate dosages of the antifungal agents can be determined by those of ordinary skill in the art of medicine by monitoring the mammal for signs of disease amelioration or inhibition, and increasing or decreasing the dosage and/or frequency of treatment as desired. The optimal amount of the antifungal compound used for treatment of conditions caused by or contributed to by fungal infection depends upon the manner of administration, the age and the body weight of the subject, and the condition of the subject to be treated. Generally, the antifungal compound is administered at a dosage of 1 to 100 mg/kg of body weight, and typically at a dosage of 1 to 10 mg/kg of body weight.

Experiments

A detailed example of the preparation of ACCase follows.

Materials and Methods

The following reagents and equipment were used. Similar reagents and equipment can be substituted for those listed herein.

| REAGENTS | Supplier |
|---|---|
| 1-Butanol | VWR Scientific EM-BX1780-5 |
| DTT dithiothreitol | VWR Scientific IB21040 |
| Bacto-Peptone | VWR Scientific DF-0118-17 |
| Bacto-Yeast Extract | VWR Scientific DF-0127-17 |
| Bacto-Agar | VWR Scientific DF-0140-01 |
| Bacto-Yeast Nitrogen Base w/o amino acids | Difco 0919-15 |
| Dimethylsulphoxide (DMSO) | VWR Scientific D-128 |
| EGTA (ethylene glycol-bis( -aminoethyl ether)-N,N,N'N'-tetraacetic acid) | Sigma Chemical Co E-0396 |
| Myristoyl CoA | Sigma Chemical Co M-9142 |
| Glucose | Sigma Chemical Co G-5767 |
| Glycerol | VWR Scientific JT2136-1 |
| Glycine | VWR Scientific EM-GX0205MB-5 |
| Hydrochloric acid, concentrated | VWR Scientific JT9535-33 |
| Magnesium chloride hexahydrate | VWR Scientific JT2444-1 |
| EDTA (ethylenediamine tetraacetic acid, disodium salt dihydrate) | VWR Scientific EM-EX0539MB-4 |
| MicroScint ™ 40 Liquid Scintillation Cocktail | Packard 6013641 |
| Micro ™ Concentrated Cleaning Solution | VWR Scientific 21830-410 |
| Ammonium Sulfate | VWR Scientific EM-1209-2 |
| D-Biotin, ImmunoPure | Pierce 29129 |
| Biotinylated BSA, ImmunoPure (Bovine Serum Albumin) | Pierce 29130 |
| PMSF Mannheim (Phenylmethylsulfonyl Fluoride) | Boehringer 837 091 |
| leupeptin | Boehringer Mannheim 1017 128 |
| antipain dihydrochloride | Boehringer Mannheim 1004 646 |
| APMSF Mannheim [(4-amidinophenyl) -methanesulfonyl fluoride hydrochloride monohydrate] | Boehringer 917 575 |
| pepstatin | Boehringer Mannheim B1359 053 |
| Immunopure ™ Monomeric Avidin/Agarose | Pierce 20228 |
| BupH ™ Phosphate Buffered Saline (0.1 M phosphate, 0.15 M NaCl, pH 7.2) | Pierce 28372 |
| Sodium Fluoride | VWR Scientific JT3688-1 |
| Potassium Chloride | VWR Scientific JT3040-1 |

| REAGENTS | Supplier |
|---|---|
| Sucrose | VWR Scientific JT4072-5 |
| TRIS Tris (hydroxymethyl) aminomethane | VWR Scientific EM-TX1530MB-2 |
| Sodium Bicarbonate | VWR Scientific JT3506-1 |
| ATP Adenosine 5'-triphosphate, disodium salt | Sigma Chemical Co A-7699 |
| Acetyl Coenzyme A Sodium Salt | Sigma Chemical Co A-2056 |
| Sodium [$^{14}$C] bicarbonate* Science 2 mCi/ml | Amersham Life CFA 3 |

| EQUIPMENT LIST | |
|---|---|
| 10 l Disposable Loops for inoculating | VWR Scientific 60872-406 |
| 10L fermenter | New Brunswick Scientific Microferm |
| fermenter | |
| Bead-Beater complete package | Biospec Products, Bartlesville, OK |
| 0.5 mm diameter glass beads | Biospec Products Bartlesville OK |
| Nalgene screw-cap polypropylene centrifuge tubes 50 ml capacity | VWR Scientific 21009-386 |
| Beckman J2-MI high-speed centrifuge | |
| Beckman JA-17 high-speed centrifuge rotor | |
| Beckman J6-MI centrifuge | |
| Beckman JS-4.0 rotor | |
| Beckman Optima ® ultracentrifuge | |
| Beckman SW41-Ti ultracentrifuge rotor | |
| Beckman Ultra-Clear centrifuge tubes 14 × 89 mm | |
| Potter-Elvehjem Tissue Grinders, Wheaton 5 ml | VWR Scientific 62400-722 |
| pH meter fitted with Tris compatible electrode | |
| Finnpipette 5-50 l 12 channel pipetman | |
| Vortex Genie 2 | VWR Scientific 58815-178 |
| 250 ml Sterilization Filter Unit, 0.2 m Cellulose Nitrate (Nalgene) | VWR Scientific 28199-111 |
| 1 L Sterilization Filter Unit, 0.2 m Cellulose Nitrate (Nalgene) | VWR Scientific 28199-268 |
| 250 ml Erlenmeyer Flask (Kimax) | VWR Scientific 28140-544 |
| Gilson P2, P100, P1000 pipetmen with tips | Rainin |
| Falcon 15 ml screw cap conical tube | VWR Scientific 21008-918 |
| Falcon 50 ml screw cap conical tube | VWR Scientific 21008-951 |
| 100 × 15 mm Sterile Disposable Petri Dishes (Falcon) | VWR Scientific 25380-069 |
| 250 ml screw-cap disposable centrifuge tubes | VWR Scientific (Corning) 21008-771 |
| 2 ml cryogenic vials (Nalgene) | VWR Scientific 66008-728 |
| 4 ml cryogenic vials, round bottom (Corning) | VWR Scientific 66021-946 |
| TopCount ™ Scintillation Counter | Packard |
| OptiPlate ™ | Packard |
| Opaque 96-well microtiter plates for TopCount | 6005190 |
| EM ColorpHast pH paper, narrow range 2.5–4.5 4.0–7.0 6.5–10 | VWR Scientific EM-9581-3 EM-9582-3 EM-9583-3 |
| 10 L Polypropylene Carboy with spigot and handles | VWR-Scientific (Nalgene) 16101-404 |

| EQUIPMENT LIST | |
|---|---|
| Ranson Slide Warmer (LabLine) [3.5 H × 28 W × 8 D"] | VWR Scientific 15160-797 |
| MultiDrop 96-well dispenser | Titertec ™ |
| Quadra 96, Model 320 Automatic Pipettor | Tomtec ™, Inc. |

Stock Solutions

1M Tris, pH 7.5 [add 500 ml dI H$_2$O to 121.4 g solid Tris base; adjust pH to 7.5 with concentrated HCl; make up to 1 L with dI H$_2$O]

10N NaOH [add 90 ml pre-chilled dI H$_2$O to 40 g pellets; stir vigorously on ice; make up to 100 ml; store in screw-cap polypropylene bottle not glass]

0.5 M Na$_2$ EDTA, pH 8.0 [46.5 g solid; suspend in 200 ml dI H$_2$O; pH; pH with 10N NaOH; make up to 250 ml; stir vigorously until dissolved]

1M MgCl$_2$ [dissolve 51 g MgCl$_2$ 6H$_2$O in 250 ml dI H$_2$O]

1M Glycine, pH 2.8 [dissolve 18.75 g Glycine in 150 ml dI H$_2$O; pH with concentrated HCl; make up to 250 ml; filter through 0.2 m using Nalgene 250 ml Sterilization filter unit]

1M NaHCO$_3$ [dissolve 8.4 g solid NaHCO$_3$ in 90 ml dI H$_2$O with vigorous stirring; make up to 100 ml]

1M DTT [dissolve 2.31 g solid DTT in 15 ml dI H$_2$O dispense in 0.75 ml aliquots and store at −20° C.]

200 mM ATP [dissolve 13.2 g in 100 ml dI H$_2$O; adjust pH to 7 with 10N NaOH (use narrow range pH paper; add 2 ml base, check pH, then 100 l increment); make up to 200 ml; store as 40 ml aliquots at −80° C. in 50 ml Falcon Tubes]

15 mM Acetyl CoA [dissolve 5*100 mg Na$_2$ (AcCoA) in 40 ml dI H$_2$O; store as 10 ml aliquots at −80° C.]

3 mM Myristoyl CoA [dissolve 5 mg myristoyl CoA in 1.7 ml DMSO Store at −20° C.]

Working Solutions (A) UltraLink™ Monomeric Avidin Column Equilibration Phosphate Buffered Saline (PBS)

0.1M phosphate, 0.15M NaCl, pH 7.2 [prepared using Pierce PubH™ mixture]

Regeneration Buffer 0.1M Glycine, pH 2.8 [30 ml 1M Stock, made up to 300 ml]

Biotin Blocking and Elution Buffer 2 mM Biotin in PBS [48.9 mg D-biotin, made up to 100 ml with PBS]

| (B) Cell Growth | |
|---|---|
| YPD growth medium (for plates) | [to make 1 liter] |
| 1% yeast extract | [10 g] |
| 2% peptone | [20 g] |
| 2% glucose | [20 g] |
| 2% agar | [20 g] |

Autoclave, cool to 60° C., dispense into disposable plastic petri dishes in flow hood. Store plates at 4° C. in plastic bag.

20% (w/v) Glucose [to Make 1 Liter]

Dissolve 200 g glucose in 1 L dI H$_2$O, autoclave.

10×SD+Uridine Growth Medium [to Make 1 Liter]

67 g yeast nitrogen base w/o amino acids 300 mg uridine Make up to 1 L with 20% (w/v) glucose solution; Filter sterilize using 0.2 micron filter bottle.

| (C) Enzyme Preparation | |
|---|---|
| Cell breakage buffer (Buffer A): | [to make 1 L] |
| 100 mM Tris, pH 7.5 | [100 ml 1 M stock] |
| 100 mM Sodium Fluoride | [4.2 g solid] |
| 1 mM EDTA | [2 ml 0.5 M stock] |
| 1 mM EGTA | [380 mg solid] |
| 10 mM DTT | [1.54 g solid] |
| 0.25 M sucrose | [86 g solid] |
| dI H$_2$O 1 L. | |
| | Store at 4° C.; Prepare Fresh |
| Column Loading buffer (Buffer B): | [to make 500 ml] |
| 50 mM Tris, pH 7.5 | [25 ml 1 M stock] |
| 10 mM DTT | [0.77 g solid] |
| 0.5 M KCl | [18.6 g solid] |
| 2 mM EDTA | [2 ml 0.5 M stock] |
| 50 ml glycerol | |
| dI H$_2$O to 500 ml. | |
| | Store at 4° C.; Prepare Fresh |
| Enzyme Storage Buffer | [to make 1 L] |
| 50 mM Tris, pH 7.0 | [50 ml 1 M Stock] |
| 1 mM EDTA | [2 ml 0.5 M stock] |
| 5 mM DTT | [0.77 g solid] |

Make up to 500 ml with dI H$_2$O; Add 500 ml glycerol. Store at 4° C.; Prepare Fresh.
Protease Inhibitors

| Inhibitor stock | Concentration Stock | Concentration in buffer | Amount/ 100 ml Buffer |
|---|---|---|---|
| PMSF | 170 g/ml | 100 mg/ml* | 170 l |
| leupeptin | 0.5 g/ml | 1 mg/ml | 50 l |
| pepstatin | 0.7 g/ml | 1 mg/ml* | 70 l |
| antipain | 50 g/ml | 10 mg/ml | 500 l |
| APMSF | 40 g/ml | 10 mg/ml | 400 l |

*In 100% methanol

| (D) High-Throughput Screen | |
|---|---|
| 20% (v/v) DMSO | [Make up 1 L] |
| ACCase Assay Buffer minus DTT | [to make up 1 L] |
| 83.33 mM Tris, pH 7.5 | [83.3 ml 1 M Stock] |
| 8.33 mM MgCl$_2$ | [8.33 ml 1 M Stock] |
| dI H$_2$O | [up to 1 L] |
| ACCase Assay Buffer [to make up 250 ml, sufficient for 25 plates] [Add 833 l 1 M DTT to 250 ml ACCase Assay Buffer minus DTT (3.33 mM DTT final concentration)] | |
| 5X Cold Substrate Buffer | |
| [to make up 390 ml, sufficient for 150 plates] | |
| 20.5 mM ATP | [40 ml 200 mM ATP, pH 7] |
| 5.13 mM NaHCO$_3$ | [2 ml 1 M NaHCO$_3$] |
| 384 M Acetyl CoA [10 ml 15 mM Acetyl CoA] | |
| dI H$_2$O | [up to 390 ml] |
| Store as 39 ml aliquots at −80° C. | |
| 5X Radiometric Substrate Buffer | |
| [to make up 40 ml, sufficient for 15 plates] | |
| 5X Cold Substrate Buffer | [39 ml; see above] |
| NaH[$^{14}$C]O$_3$ | [1 ml 2 mCi/ml Stock] |
| Prepare immediately before addition to screening plates, as $^{14}$C bicarbonate exchanges with atmospheric CO$_2$ | |
| Stop Solution (2N HCl) | [to make 10 L] |
| [add 1.67 L concentrated HCl to 7 L pre-chilled dI H$_2$O on ice slowly, with stirring; Make up to 10 L | |

-continued

| (D) High-Throughput Screen | |
|---|---|
| with dI H$_2$O] | |
| Store in a 10 L Nalgene Carboy at Room temp. | |

Methods (A) Preparation of Enzyme from *A. fumigatus*

(1) Growth of Cells

A strain of *A. fumigatus* was stored as a glycerol stock in 2 ml cryovials at −80° C. Cells were streaked out onto YPD plates using a 10 l Loop and incubated for 24–48 hours at 30° C.

The strain of *A. fumigatus* from plates was inoculated into 50 ml of SD+uridine and incubated overnight, with shaking, at 30° C. Cells were subcultured into 250 ml SD+uridine and shaken at 30° C. for 8–9 hours. This culture was used to inoculate (in parallel) two 10 L fermenters containing SD+uridine to a starting OD$_{600}$ of 0.01 to 0.015. [Fermenters were autoclaved containing 9 L of dI water, and 1 L of 10×SD+uridine was added 30 minutes before inoculation.] The cells were grown overnight at 30° C. to a final OD$_{600}$ of 2.0–2.5 (mid-exponential phase) and harvested by centrifugation (J6-MI centrifuge, JS-4.0 rotor, 3000 rpm for 10 minutes). The fermentation takes about 17 hours, and the harvest time can be calculated (accuracy±half hour) based on the inoculation OD, and lag and doubling times. In a typical run, fermenters were inoculated at 6 pm and harvested at 10 am the following day. Lag time was ≦15 minutes and doubling time was 2 hours. The second fermenter was inoculated to a slightly lower OD, such that cells were ready for harvesting about 45 minutes to 1 hour after the first was ready (to allow for the time it takes to harvest the first). About 160 g of packed cells were obtained from two 10 L fermenters.

After harvesting in Corning 250 ml disposable centrifuge tubes, cells were immediately frozen at −80° C. and stored until processing.

(2) Lysis of Cells and Preparation of 40% Ammonium Sulfate Precipitate

All operations were performed at 4° C. Protease inhibitors were added to Buffer A (cell breakage buffer) and one volume of this mixture was added to one volume of packed cells (75 g cells yields 150 ml of suspension; sufficient to fill the bead-beater chamber). The cells were resuspended by brief vortexing, and the cell suspension was transferred to the bead-beater chamber (already half-filled with prewetted glass beads). The glass bead/cell suspension mixture was stirred with a glass rod to remove trapped air. The bead-beater chamber was assembled, displacing as much air as possible from the chamber. The cells were ruptured by 2×1 minute pulses of the bead beater, separated by 4 minutes cooling between pulses. The lysate was transferred by decanting (to remove glass beads) into a pre-cooled 250 ml Erlenmeyer flask. Fresh PMSF and pepstatin were added, and the lysate was transferred to 50 ml screw-cap centrifuge tubes and centrifuged at 10,000×g for 20 minutes to remove unbroken cells, cell wall fragments and mitochondria. The supernatant was centrifuged at 100,000×g for 60 minutes (Beckman Ultra-Clear 25×89 mm; using the SW-28 rotor) and decanted into a pre-chilled 250 ml Erlenmeyer Flask. Solid ammonium sulfate was gradually added to the high-speed supernatant to 40% saturation (24.2 g/100 ml). This mixture was left for 30 minutes at 4° C. to equilibrate, with occasional gentle swirling. The ammonium sulfate precipitate was collected by centrifugation at 15,000×g for 30 minutes, discarding the supernatant. The resulting pellets can be left at 4° C. overnight in the centrifuge tubes for resuspension the following day (ensure pellets do not dry out by adding 5 ml Buffer A containing 40% Saturated Ammonium Sulfate). It is, however, preferable to carry the protein through the column purification step without stopping.

The lysis procedure can be repeated twice in a day, enabling the processing of 2 fermenters worth of cells at once. Glass beads can be rinsed with 2% Micro™ cleaning solution and re-used as necessary.

(3) Column Chromatography on Pierce ImmunoPure™ Monomeric Avidin Gel (a) Pretreatment and Equilibration of Column The column at room temperature. The gel was diluted to 33% v/v with dI $H_2O$ and the corresponding slurry was used to pour the column (convenient disposable columns and instructions were supplied with the resin). After allowing the gel to settle (the column was stoppered at the bottom during pouring) a plastic frit was gently layered on top of the bed using the appropriate size serum separator provided with the column. The column was equilibrated after pouring with 2×2 CV (column volumes) phosphate buffered saline (made up using Pierce BupH™ PBS pack). In order to block all the tight biotin-binding sites in the resin, the column was washed with Biotin Blocking and Elution Buffer (3×1 CV). This was followed with 3×2 CV Regeneration Buffer, which removes biotin from the loose-binding sites. The column was washed with 2×2 CV PBS for storage, and can be tested for binding capacity using biotinylated BSA (preferably it should be regenerated after measurement).

A 5-ml column is sufficient to purify all the enzyme from two fermenters worth of cells. Monomeric avidin Gel is stored in PBS (33% v/v gel) at 4° C. before use.

(b) Purification of Biotin-containing Proteins

All operations were performed at 4° C. The ammonium sulfate precipitate was taken up in a minimum volume of Buffer B+protease inhibitors. A 5 ml Potter-Elvehjem homogenizer was used to facilitate the resuspension of the pellets. After homogenization, the protein solution was centrifuged (100,000×g, 60 minutes) to remove any insoluble material. Ammonium sulfate precipitates from two fermenters worth of cells can be resuspended in about 48 ml Buffer B, which was sufficient liquid to fill 4 ultracentrifuge tubes (16×89 mm, SW41-Ti rotor). Biotinylated proteins were batch-loaded onto monomeric avidin gel by adding 15 ml 33% gel slurry to the combined hi-speed supernatant, and gently shaking the mixture in 50 ml Falcon tubes on a rotating shaker (60 rpm) for 1.5 hours (4° C.). The mixture was immediately poured into a 10 ml column (supplied by Pierce with the gel). After allowing time for the gel to settle, the resin was resuspended in 1 CV Buffer B by capping the column and gently shaking. It was then left at 4° C. to settle out again. After 45 minutes, the gel has formed a bed and a plastic frit was gently placed on top of the column to prevent drying. The column was washed with about 5 CV of Buffer B (until the flow-through was essentially devoid of protein, as judged by Bradford Assay). ~1 CV 2 mM biotin in buffer B was applied to the column and the column capped for 1 hour to allow for exchange of bound proteins with free biotin. Proteins were eluted with 2 mM biotin in buffer B, monitoring for protein with the Bradford assay. Fractions were collected until no more protein eluted, and pooled. Pooled fractions were dialyzed overnight against Storage Buffer (which contains 50% glycerol). Protein was stored at −20° C.

Each enzyme preparation was tested for activity in the radiometric assay described below. In addition, the minimum amount of enzyme required for acceptable signal to noise and linearity in the assay (over a 45-minute time period) was determined for each batch. Several batches can be pooled and realiquoted, but the enzyme was re-assayed under the same conditions that will be used in the screen to ensure signal to noise and linearity were in the acceptable range.

(A) High-throughput Screen (I) Running the Screen

Reagents and amounts are summarized in the following table. Screening is performed in accordance with the protocol described in detail below.

| Reagent | Max (100%) D1 D7 | | Min (0%) D3 D9 | 50% Test |
|---|---|---|---|---|
| | | D2 D8 | | |
| | | Volume (l) | | |
| 20% DMSO | 20 | 20 | 20 | 20 |
| Diluted enzyme in Assay Buffer | 60 | 0 | 60 | 60 |
| Assay Buffer | 0 | 60 | 0 | 0 |
| 5X Radioactive Substrate Buffer | 20 | 20 | 20 | 20 |
| Myristoyl CoA (3 mM in DMSO) | 0 | 0 | 1 | 0 |
| Test compound* | 0 | 0 | 0 | 5 M final conc. |

*Test Compound stock diluted in BuOH 1:10; 25 l dried in assay plate in hood prior to addition of assay buffer. Well contains 0.5 nmol of each test compound (20/well) in 2.5 l 100% DMSO.

Potency of inhibitors can be quantified with respect to positive (no enzyme; 100% inhibition) and negative (no inhibitor; 0% inhibition) controls. The following formula can be used:

% Inhibition={1−[$A_{450}$−(positive control)]/[(negative control)−(positive control)]}*100

(B) Radiometric Assay for Acetyl CoA Carboxylase Concentrations of Assay Components

| Component | Stock Concentration | Final Concentration |
|---|---|---|
| HEPES, pH 7.5 | 83.33 mM* | 50 mM |
| $MgCl_2$ | 8.333 mM* | 5 mM |
| DTT | 3.33 mM* | 2 mM |
| ATP | 20 mM† | 4 mM |
| Acetyl CoA | 375 M† | 75 M |
| $NaHCO_3$ | 5 mM† | 1 mM |
| NaH[$^{14}$C]$O_3$ | 2 mCi/ml | 10 Ci/ml‡ |

*in ACCase Assay Buffer
†in 5X Substrate
‡10 Ci/mol Buffer 20 l of 20% DMSO are dispensed into all wells of each microtiter plate using a Titertec™ multidrop. 1 l of 3 mM Myristoyl CoA in DMSO is added to appropriate control wells (D3 and D9). 60 l enzyme (pre-diluted with ACCase Assay Buffer) are added to all wells by the Titertec™, covering wells with adhesive foil for no-enzyme controls (D2 and D8). In the control wells, enzyme solution forms a bead on top of the foil, and does not splash into adjacent wells. After enzyme addition, the bead on top of the foil is removed with a KimWipe™ and the foil removed for subsequent additions. 60 l of ACCase Assay Buffer (no enzyme) are then added to wells D2 and D8.

The 5× Radiometric Substrate Buffer is prepared from 5× Cold Substrate Buffer by the addition of NaH[$^{14}$C]O$_3$.

Immediately after radioactive bicarbonate is added, the assay reaction is initiated by addition of 20 l 5× radiometric substrate buffer to each well using a Titertec™ MultiDrop dispenser. The Titertec™ is rinsed with 2N HCl (stop solution) immediately after dispensing the substrate buffer in preparation for the termination step of the assay. The reaction is stopped after a 40 minute incubation period (room temperature), by the addition of 100 l Stop Solution (using the Titertec™).

The plates are dried overnight at 45° C. on a Slide Warmer. 10 plates can be laid out on each slide warmer. Using the Titertec™, 100 l dI H$_2$O are added to the dried wells to resolubilize the product, and 80 l of this material are transferred to an OptiPlate™. The transfer step is accomplished using the Tomtec™ automatic dispenser. 150 l of MicroScint™40, are added by Titertec™ (dedicated dispensing head). The plates are counted (after 12 hours equilibration) using a Packard TopCount (count 60 seconds; 1 minute delay before reading plate). Data are saved to a file for analysis by Microsoft Excel™.

Purification of ACCase from Crude Lysates $^{14}$C-labeled bicarbonate and ammonium sulfate are obtained from ICN Biomedicals. All supplies and gels for polyacrylamide gel electrophoresis and streptavidin blots are purchased from Bio-Rad. All other fine chemicals are purchased from Sigma. Sepharose CL-4B is purchased from Pharmacia. Promega Soft-Link, Soft Release avidin affinity resin is purchased from Fisher Scientific.

A fungal lysate is prepared in 225 mM mannitol, 75 mM sucrose, 10 mM Tris/HCl pH 7.5, 0.05 mM EDTA, 5 mM potassium citrate, 2.5 mM MnCl$_2$, 10 mg/l each of aprotinin, leupeptin and antitrypsin (buffer A) is filtered through glass wool and powdered ammonium sulfate is added slowly, with stirring, to 35% saturation (200 g ammonium sulfate/l). Following 45 minutes of continued stirring, precipitated protein is collected by centrifugation (30 min, 17000×g). The precipitate is gently resuspended with stirring in a minimum volume of 100 mM Tris/HCl, pH 7.5, 0.5 M NaCl, 1.0 mM EDTA, 0.1 mM dithiothreitol and 10% glycerol (buffer B). Insoluble material is then removed by centrifugation (20 min, 40000×g) and the clarified supernatant dialyzed for 3 hours against 150 vol. 100 mM Tris/HCl, 0.5 M NaCl, 1.0 mM EDTA, 0.1 mM dithiothreitol and 5% glycerol (buffer C) to remove citrate.

The dialyzed suspension (approximately 30 ml) is then shaken with 40 ml affinity-column material [prepared by the procedure of Beaty and Lane 1982 (J Biol Chem 257: 924–929] and 30 ml buffer C for 3 hours, rinsed in a fritted funnel using 2 liters buffer C with stirring, and packed into a column with continual rinsing (10–15 ml/hour) until a stable baseline is achieved. The effluent from the column is monitored at 280 nm using an ISCO UA-6 absorbance detector. Avidin-bound material is eluted with buffer C (0.2 mM in biotin) at 5–8 ml/hour.

ACCase Assay

Fungal acetyl-CoA carboxylase is assayed by a modification of the $^{14}$CO$_2$ fixation assay of Thampy and Wakil (1985 J Biol Chem 260: 6318–6323) as follows: Purified enzyme (0.05 g) is added to a reaction mix (50 mM Hepes, pH 7.5, 1.5 mM magnesium sulfate, 2.0 mM dithiothreitol, 0.25 mM acetyl-CoA, 4.0 mM ATP, 12.5 mM KHCO$_3$ (2×10$^6$ cpm NaH[$^{14}$C]O$_3$), 0.75 g/l fatty-acid-free bovine serum albumin, 20 mM sodium citrate, 20 mM magnesium acetate in a total volume of 200 l ) at 37° C. for 2 min. Reactions are terminated by the addition of 50 l 5 M HCl. Aliquots (200 l) are transferred and evaporated to dryness (80° C. in a hood under a gentle air stream). After cooling, distilled water (400 l) is added followed by the addition of 5.5 ml Scintiverse II (Fisher). Radioactivity is determined in a Beckman LS 6500 Scintillation system. Assay blanks consisted of a standard assay with HCl added prior to enzyme. Typical background activity averaged 50 cpm. One unit activity is equal to 1 mol NaH[$^{14}$C]O$_3$ incorporated into acid-stable material/minute at 37° C. The specific activity is given in units/mg protein.

Protein Determination

Protein is determined using the Bio-Rad Protein assay dye kit using bovine serum albumin as a standard.

Polyacrylamide Gel Electrophoresis

Protein samples are prepared by diluting in 62.5 mM Tris, pH 6.8, 10% glycerol, 2.5% (mass/vol.) SDS, 5% (by vol.) 2-mercaptoethanol, 0.025% (mass/vol.) Bromphenol blue (SDS sample buffer), and heating (95° C., 4 min). Polyacrylamide gel electrophoresis is performed with the Bio-Rad Mini-Protean II Dual Slab Vertical Electrophoresis System using Mini-Protean II 4–15% gradient precast gels (Bio-Rad). Gels are run in the presence of 0.1% SDS, 25 mM Tris, 192 mM glycine, pH 8.3, at 200 V for 60 min.

Gel Staining

Pooled column fractions are run parallel to high-range molecular-mass standards (silver staining) and to biotinylated high-range molecular-mass standards (Western blotting). Both sets of standards are obtained from Bio-Rad. Gels (run concurrently with those used for silver staining) are stained with silver staining according to established procedures. Reagents for silver staining are obtained in the form of a kit (Sigma).

Western Blotting

Proteins are transferred to nitrocellulose (Mini Trans-Blot Electrophoretic Transfer system from Bio-Rad) as follows. Gels are sandwiched next to nitrocellulose membranes in buffer (25 mM Tris, 192 mM glycine, 20% methanol, pH 8.3) overnight using a cooling well (30 V, model 1000/500 power supply, Bio-Rad).

Biotin-containing proteins are detected by streptavidin-alkaline-phosphatase conjugate (Bio-Rad). Streptavidin-specific protein is visualized calorimetrically using color reagents supplied in a streptavidin-alkaline-phosphatase conjugate substrate kit obtained from Bio-Rad. Membranes are stored in distilled H$_2$O.

Antibodies

Antibodies can be raised against ACCase enzyme of the present invention by conventional techniques.

Northern Hybridization and Probe Preparation

Northern blots, obtained from Clontech (Clontech Laboratories, 1020 East Meadow Circle, Palo Alto, Calif., 94303, USA), are prehybridized for 1 hour in Expresshyb hybridization solution (Clontech—Clontech Laboratories, 1020 East Meadow Circle, Palo Alto, Calif., 94303, USA) at 55° C. before a radiolabelled ACCase fragment (DNA is labelled using the Megaprime random labelling system (Amersham (Amersham place, Little Chalfont, Bucks, HP7 9NA UK}) strictly following the manufacturers instructions with 50 Ci of $^{32}$P-dATP) is added to fresh Expresshyb and hybridized to the blot overnight at 55° C., with gentle shaking. Blots are then washed 3× at room temperature for 10 minutes each in 2×SSC (150 mM NaCl, 30 mM Nacitrate) followed by 2 washes in 0.2×SSC (15 mM NaCl, 3mM Nacitrate) at 55° C. for 20 minutes each. Blots are then exposed to autoradiographic film.

Polymerase Chain Reactions (PCR)

PCR reactions are performed using standard reagents and conditions. Briefly, all reaction buffers and enzymes are obtained in kit format from either Clontech {Clontech Laboratories, 1020 East Meadow Circle, Palo Alto, Calif., 94303, USA} (for rapid amplification of cDNA ends (RACE) reactions) or from Life Technologies (3 Fountain Drive, Inchinnan Business Park, Paisley, PA4 9RF UK) for standard PCR. Oligonucleotides are obtained from a commercial supplier (OSWEL DNA services, Lab 5005, Medical And Biological Sciences Building, University of Southampton, Bolderwood, Bassett Crescent East, Southampton, SO16 7PX UK) and used at a concentration of 400 nM. Reactions are performed on a MJ Research PTC-200 thermal cycler, using cycling parameters as recommended by the manufacturer of the kit being used.

Cloning of PCR Products

PCR derived DNA fragments are cloned using the TOPO cloning system (Cat No. K3001-0-1) supplied by Invitrogen (De Schelp 12, 9351 NV Leek, The Netherlands), following the methods as outlined in the manufacturers method book and using the reagents as supplied.

Other Embodiments

It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims. For example, other art-known assays to detect interactions of test compounds with proteins, or to detect inhibition of fungal growth also can be used with the ACCase gene. The invention also includes methods of making a pharmaceutical composition for use in inhibiting *A. fumigatus*. Specifically, the method includes formulating a pharmaceutically acceptable excipient with an antifungal agent, such as those described herein.

What is claimed is:

1. An isolated nucleic acid molecule selected from the group consisting of:
   (a) a cDNA molecule that encodes a polypeptide comprising the amino acid sequence of SEQ ID NO:2;
   (b) a cDNA molecule that encodes a polypeptide comprising at least 150 contiguous amino acids of SEQ ID NO:2;
   (c) a cDNA molecule that encodes an allelic variant of a polypeptide comprising the amino acid sequence of SEQ ID NO:2, wherein the cDNA molecule hybridizes under stringent conditions to a nucleic acid molecule consisting of the nucleotide sequence of SEQ ID NO:1, or the complement of SEQ ID NO:1.

2. An isolated nucleic acid molecule selected from the group consisting of:
   (a) a nucleic acid molecule comprising the nucleotide sequence of SEQ ID NO:1;
   (b) a nucleic acid molecule comprising the nucleotide sequence of SEQ ID NO:1, wherein the thymidine deoxynucleotides have been replaced by uracil ribonucleotides;
   (c) a nucleic acid molecule that is complementary to (a) or (b); and
   (d) fragments of (a), (b) or (c) that comprise at least 300 contiguous nucleotides of SEQ ID NO:1 or the complement of SEQ ID NO:1.

3. An isolated nucleic acid molecule selected from the group consisting of:
   (a) a nucleic acid molecule comprising a nucleotide sequence which is at least about 85% identical to the nucleotide sequence of SEQ ID NO:1, or a complement thereof, wherein the percent identity is calculated using the GAP program in the OCG software package, using a gap weight of 5.000 and a length weight of 0.100;
   (b) a nucleic acid molecule comprising a nucleotide sequence tat hybridizes to a nucleic acid molecule consisting of the nucleotide sequence of SEQ ID NO:1 under stringent conditions, or a complement thereof; and
   (c) a nucleic acid molecule comprising a nucleotide sequence that hybridizes under stringent conditions to a nucleic acid molecule consisting of the nucleotide sequence of the cDNA insert of a plasmid deposited with the ATCC as Accession Number 207005, 207006, 207007, 207008, or 207009, or a complement thereof, wherein the nucleic acid molecules in (a), (b), and (c) encode polypeptides that catalyze the carboxylation of acetyl CoA.

4. A vector comprising the nucleic acid molecule of any one of claim 1, 2, or 3.

5. A nucleic acid molecule of any one of claim 1, 2, or 3, further comprising a nucleic acid sequence encoding a heterologous polypeptide.

6. A host cell that contains the nucleic acid molecule of any one of claim 1, 2, or 3.

7. A host cell of claim 6, wherein the cell is a mammalian host cell.

8. A host cell of claim 6, wherein the cell is a non-mammalian host cell.

9. A method for producing a polypeptide comprising culturing the host cell of claim 6 under conditions in which the nucleic acid molecule is expressed, wherein the polypeptide is selected from the group consisting of:
   (a) a polypeptide comprising the amino acid sequence of SEQ ID NO:2;
   (b) a polypeptide comprising at least 150 contiguous amino acids of SEQ ID NO:2; and
   (c) an allelic variant of a polypeptide comprising the amino acid sequence of SEQ ID NO:2, wherein the polypeptide is encoded by a nucleic acid molecule that hybridizes under stringent conditions to a nucleic acid molecule comprising SEQ ID NO:1.

* * * * *

SEQUENCE LISTING

<160> NUMBER OF SEQ ID NOS: 2

<210> SEQ ID NO 1
<211> LENGTH: 6359
<212> TYPE: DNA
<213> ORGANISM: Aspergillus fumigatus
<220> FEATURE:
<221> NAME/KEY: CDS
<222> LOCATION: (1)...(6048)

<400> SEQUENCE: 1

| | | | | | | | | | | | | | | | | |
|---|---|---|---|---|---|---|---|---|---|---|---|---|---|---|---|---|
| gat | ttt | atc | atg | aag | ttg | gct | ggc | aat | gcc | cgg | cat | ctg | gaa | gtc | cag | 48 |
| Asp | Phe | Ile | Met | Lys | Leu | Ala | Gly | Asn | Ala | Arg | His | Leu | Glu | Val | Gln | |
| 1 | | | | 5 | | | | | 10 | | | | | 15 | | |

| ctg | ctg | gct | gat | cag | tat | gga | aac | aac | atc | tcc | ctg | ttc | ggc | aga | gac | 96 |
|---|---|---|---|---|---|---|---|---|---|---|---|---|---|---|---|---|
| Leu | Leu | Ala | Asp | Gln | Tyr | Gly | Asn | Asn | Ile | Ser | Leu | Phe | Gly | Arg | Asp | |
| | | | 20 | | | | | 25 | | | | | 30 | | | |

| tgc | tcc | gta | cag | cgt | cgt | cac | cag | aag | att | atc | gag | gag | gcc | ccc | gtc | 144 |
|---|---|---|---|---|---|---|---|---|---|---|---|---|---|---|---|---|
| Cys | Ser | Val | Gln | Arg | Arg | His | Gln | Lys | Ile | Ile | Glu | Glu | Ala | Pro | Val | |
| | | 35 | | | | | 40 | | | | | 45 | | | | |

| acc | atc | gcc | aag | ccc | gcc | acg | ttc | cag | gcc | atg | gag | cgt | gcg | gct | gtc | 192 |
|---|---|---|---|---|---|---|---|---|---|---|---|---|---|---|---|---|
| Thr | Ile | Ala | Lys | Pro | Ala | Thr | Phe | Gln | Ala | Met | Glu | Arg | Ala | Ala | Val | |
| 50 | | | | | 55 | | | | | 60 | | | | | | |

| agc | ctc | gga | aag | ctg | gtt | ggt | tac | gtc | tcc | gcg | ggt | acc | gtc | gag | tac | 240 |
|---|---|---|---|---|---|---|---|---|---|---|---|---|---|---|---|---|
| Ser | Leu | Gly | Lys | Leu | Val | Gly | Tyr | Val | Ser | Ala | Gly | Thr | Val | Glu | Tyr | |
| 65 | | | | 70 | | | | | 75 | | | | | 80 | | |

| ctg | tac | tcg | cac | gcc | gat | gac | aag | ttc | tac | ttc | ctc | gag | ttg | aac | cct | 288 |
|---|---|---|---|---|---|---|---|---|---|---|---|---|---|---|---|---|
| Leu | Tyr | Ser | His | Ala | Asp | Asp | Lys | Phe | Tyr | Phe | Leu | Glu | Leu | Asn | Pro | |
| | | | 85 | | | | | 90 | | | | | 95 | | | |

| cgt | ctt | cag | gtc | gag | cac | ccc | acc | acc | gaa | atg | gtc | tcc | ggt | gtc | aac | 336 |
|---|---|---|---|---|---|---|---|---|---|---|---|---|---|---|---|---|
| Arg | Leu | Gln | Val | Glu | His | Pro | Thr | Thr | Glu | Met | Val | Ser | Gly | Val | Asn | |
| | | | | 100 | | | | | 105 | | | | | 110 | | |

| ctg | cca | gcc | gcc | caa | ttg | caa | atc | gcc | atg | ggt | atc | cct | ctg | cac | cgc | 384 |
|---|---|---|---|---|---|---|---|---|---|---|---|---|---|---|---|---|
| Leu | Pro | Ala | Ala | Gln | Leu | Gln | Ile | Ala | Met | Gly | Ile | Pro | Leu | His | Arg | |
| | | | 115 | | | | | 120 | | | | | 125 | | | |

| atc | cgt | gac | atc | cgt | ctg | ctc | tac | ggg | gtt | gac | ccc | aac | acc | tcg | tcc | 432 |
|---|---|---|---|---|---|---|---|---|---|---|---|---|---|---|---|---|
| Ile | Arg | Asp | Ile | Arg | Leu | Leu | Tyr | Gly | Val | Asp | Pro | Asn | Thr | Ser | Ser | |
| | | 130 | | | | | 135 | | | | | 140 | | | | |

| gag | att | gac | ttc | gac | ttc | tcc | agc | gaa | gag | agc | ttc | aaa | acg | cag | cgc | 480 |
|---|---|---|---|---|---|---|---|---|---|---|---|---|---|---|---|---|
| Glu | Ile | Asp | Phe | Asp | Phe | Ser | Ser | Glu | Glu | Ser | Phe | Lys | Thr | Gln | Arg | |
| 145 | | | | | 150 | | | | | 155 | | | | | 160 | |

-continued

| | |
|---|---|
| cgc cct cag ccc aag gga cac acg acc gcc tgc cgt atc act tcc gaa<br>Arg Pro Gln Pro Lys Gly His Thr Thr Ala Cys Arg Ile Thr Ser Glu<br>165                      170                  175 | 528 |
| gat ccc ggc gaa ggt ttc aag ccc tcc agc ggt acc atg cat gaa ttg<br>Asp Pro Gly Glu Gly Phe Lys Pro Ser Ser Gly Thr Met His Glu Leu<br>180                      185                  190 | 576 |
| aac ttc cgc agt tcg tcc aac gtc tgg ggt tac ttc tcc gtc ggt acc<br>Asn Phe Arg Ser Ser Ser Asn Val Trp Gly Tyr Phe Ser Val Gly Thr<br>           195                  200                  205 | 624 |
| gcc ggt ggt atc cac agc ttc tcc gac agc cag ttc ggt cac atc ttt<br>Ala Gly Gly Ile His Ser Phe Ser Asp Ser Gln Phe Gly His Ile Phe<br>210                      215                  220 | 672 |
| gcc tac ggt gag acg cgt tcc gcg tcg cgg aaa cac atg gtt gtc gct<br>Ala Tyr Gly Glu Thr Arg Ser Ala Ser Arg Lys His Met Val Val Ala<br>225                      230                  235                  240 | 720 |
| ctg aag gag ttg agc atc cgg ggt gac ttc cgc acg aca gtc gag tac<br>Leu Lys Glu Leu Ser Ile Arg Gly Asp Phe Arg Thr Thr Val Glu Tyr<br>           245                  250                  255 | 768 |
| ctg atc aag cta ctg gag acc cct gct ttc gag gat aac acc atc acc<br>Leu Ile Lys Leu Leu Glu Thr Pro Ala Phe Glu Asp Asn Thr Ile Thr<br>260                      265                  270 | 816 |
| act gga tgg ctg gat cag ctc atc tcg aac aag ctg acc gca gag cgt<br>Thr Gly Trp Leu Asp Gln Leu Ile Ser Asn Lys Leu Thr Ala Glu Arg<br>           275                  280                  285 | 864 |
| ccg gat ccc atc gtg gct gtt ctg tgc ggt gcg gtg acc aag gct cac<br>Pro Asp Pro Ile Val Ala Val Leu Cys Gly Ala Val Thr Lys Ala His<br>290                      295                  300 | 912 |
| ctg gcc agc gaa ggc ggt gtc gag gag tat cgc aag ggc ctc gaa aag<br>Leu Ala Ser Glu Gly Gly Val Glu Glu Tyr Arg Lys Gly Leu Glu Lys<br>305                      310                  315                  320 | 960 |
| ggt cag gtg ccc tcc aat gac gtc ctc aag acc gtc ttc ccc gtg gac<br>Gly Gln Val Pro Ser Asn Asp Val Leu Lys Thr Val Phe Pro Val Asp<br>                    325                  330                  335 | 1008 |
| ttc atc tac gag ggc cag cgg tac aag ttc acc gca acc aga gcc ggc<br>Phe Ile Tyr Glu Gly Gln Arg Tyr Lys Phe Thr Ala Thr Arg Ala Gly<br>340                      345                  350 | 1056 |
| ttg gac agc tac cac ctg ttc atc aac gga tcc aag tgc tcg gtc ggt<br>Leu Asp Ser Tyr His Leu Phe Ile Asn Gly Ser Lys Cys Ser Val Gly<br>           355                  360                  365 | 1104 |
| gtc cgt gct ctg gcc gac ggt ggc ctg ctt gtg ctc ctg aac ggt cgt<br>Val Arg Ala Leu Ala Asp Gly Gly Leu Leu Val Leu Leu Asn Gly Arg<br>370                      375                  380 | 1152 |
| agt cac aac gtc tac tgg aag gag gaa gcg gct gca act cgc ctg agt<br>Ser His Asn Val Tyr Trp Lys Glu Glu Ala Ala Ala Thr Arg Leu Ser<br>385                      390                  395                  400 | 1200 |
| gtc gac gga aag acg tgc ttg ctg gag cag gag aat gat cct act cag<br>Val Asp Gly Lys Thr Cys Leu Leu Glu Gln Glu Asn Asp Pro Thr Gln<br>                    405                  410                  415 | 1248 |
| ctt cgc tcc ccg tcc ccc gga aag ctt gtc aag ttc acg gtc gag aac<br>Leu Arg Ser Pro Ser Pro Gly Lys Leu Val Lys Phe Thr Val Glu Asn<br>420                      425                  430 | 1296 |
| ggc gag cac gtc aag gct ggt cag gcc ttc gcc gaa gtc gag gtc atg<br>Gly Glu His Val Lys Ala Gly Gln Ala Phe Ala Glu Val Glu Val Met<br>           435                  440                  445 | 1344 |
| aag atg tac atg ccc ctg att gca cag gaa gat ggt att gtt cag ctc<br>Lys Met Tyr Met Pro Leu Ile Ala Gln Glu Asp Gly Ile Val Gln Leu<br>450                      455                  460 | 1392 |
| atc aag cag cct ggt tcc acc ctc gag gcc ggt gac atc ctc ggt att<br>Ile Lys Gln Pro Gly Ser Thr Leu Glu Ala Gly Asp Ile Leu Gly Ile | 1440 |

-continued

```
     465                 470                 475                 480
ctc gct ctg gat gac cca tct cgt gtc aca cat gcc cag cct ttt acc       1488
Leu Ala Leu Asp Asp Pro Ser Arg Val Thr His Ala Gln Pro Phe Thr
                    485                 490                 495 gga cag ctg ccc gac ctt ggt ccc ccg caa gtg gtc ggt aac aag cct       1536
Gly Gln Leu Pro Asp Leu Gly Pro Pro Gln Val Val Gly Asn Lys Pro
                500                 505                 510 cct cag aga ttc tcc ctc ctc cac agt att ctc gag aac atc ctc atg       1584
Pro Gln Arg Phe Ser Leu Leu His Ser Ile Leu Glu Asn Ile Leu Met
            515                 520                 525 ggc tat gac aac caa gtt atc atg aac acc act ctg aag gag ctg gtt       1632
Gly Tyr Asp Asn Gln Val Ile Met Asn Thr Thr Leu Lys Glu Leu Val
        530                 535                 540 gag gtt ttg cgg gat cct gaa ctt ccc tac ggt gaa tgg aac gct cag       1680
Glu Val Leu Arg Asp Pro Glu Leu Pro Tyr Gly Glu Trp Asn Ala Gln
545                 550                 555                 560 tct tct gcc ctt cat tct cgt atg ccc cag aag ctg gac gct cag ctt       1728
Ser Ser Ala Leu His Ser Arg Met Pro Gln Lys Leu Asp Ala Gln Leu
                565                 570                 575 cag agc atc gtc gac aag gct cac gcc aga aag gcc gag ttc ccc gcc       1776
Gln Ser Ile Val Asp Lys Ala His Ala Arg Lys Ala Glu Phe Pro Ala
                580                 585                 590 aag cag ctg cag aag act atc tcc cgc ttc atc gag gag aac gtc aac       1824
Lys Gln Leu Gln Lys Thr Ile Ser Arg Phe Ile Glu Glu Asn Val Asn
            595                 600                 605 cca gcc gac gcc gag atc ctc aaa acc act ctc ctc cct ctt cag cag       1872
Pro Ala Asp Ala Glu Ile Leu Lys Thr Thr Leu Leu Pro Leu Gln Gln
        610                 615                 620 gtc atc acc aag tac atg gat ggc ctg aag gcc cac gag ttc aac gtc       1920
Val Ile Thr Lys Tyr Met Asp Gly Leu Lys Ala His Glu Phe Asn Val
625                 630                 635                 640 ttc gct gga ttg ctg gag cag tac tac aag gtc gag agc ctc ttc tct       1968
Phe Ala Gly Leu Leu Glu Gln Tyr Tyr Lys Val Glu Ser Leu Phe Ser
                645                 650                 655 ggc cgc aac atc cgc gac gaa gat gcc atc ctg aag ctc aga gaa gag       2016
Gly Arg Asn Ile Arg Asp Glu Asp Ala Ile Leu Lys Leu Arg Glu Glu
                660                 665                 670 cac aag gac gat att ggc agc gtc gtt cag ctg gta ctg tcc cac agc       2064
His Lys Asp Asp Ile Gly Ser Val Val Gln Leu Val Leu Ser His Ser
            675                 680                 685 cgt att ggc gcg aag aac aac ctc att ttg gcc atc ctg gcc atg tac       2112
Arg Ile Gly Ala Lys Asn Asn Leu Ile Leu Ala Ile Leu Ala Met Tyr
        690                 695                 700 cgc ccc aac cag cct ggt gct ggc aat gtc gca aag tac ttc aag ccc       2160
Arg Pro Asn Gln Pro Gly Ala Gly Asn Val Ala Lys Tyr Phe Lys Pro
705                 710                 715                 720 gtc ctg aag aag ctc act gaa ctt gag tcg cgg ccc gcc gcc aag gtc       2208
Val Leu Lys Lys Leu Thr Glu Leu Glu Ser Arg Pro Ala Ala Lys Val
                725                 730                 735 acc ctc aag gcc cgt gag gtc ctc atc cag tgt gcg ctt ccc tcc atg       2256
Thr Leu Lys Ala Arg Glu Val Leu Ile Gln Cys Ala Leu Pro Ser Met
                740                 745                 750 gag gag cgt atg tct cag atg gaa ctc att ctg cgc tcc tct gtt gtc       2304
Glu Glu Arg Met Ser Gln Met Glu Leu Ile Leu Arg Ser Ser Val Val
            755                 760                 765 gaa tcc cga tac gga gag acc ggt tgg gac cac cgg gag ccc gaa ttc       2352
Glu Ser Arg Tyr Gly Glu Thr Gly Trp Asp His Arg Glu Pro Glu Phe
        770                 775                 780 tcc gtc ctc aag gaa gtg gtg gac tcc aag tac acc gtc ttc gac gtc       2400
```

```
Ser Val Leu Lys Glu Val Val Asp Ser Lys Tyr Thr Val Phe Asp Val
785                 790                 795                 800 ctg acc cga ttc ttc gtt cat ccg gac cct tgg gtc acc ctg gct gct      2448
Leu Thr Arg Phe Phe Val His Pro Asp Pro Trp Val Thr Leu Ala Ala
                805                 810                 815 ctc gag gtc tac att cgc cgt gcc tac agg gcc tat aca ctg aag ggt      2496
Leu Glu Val Tyr Ile Arg Arg Ala Tyr Arg Ala Tyr Thr Leu Lys Gly
            820                 825                 830 att cag tac tac ccc gat gga gaa gtc ccc ctg gtc tcc tgg gac ttt      2544
Ile Gln Tyr Tyr Pro Asp Gly Glu Val Pro Leu Val Ser Trp Asp Phe
        835                 840                 845 acg cta ggc aag ctt gga caa ccg gag ttc ggt tcc gtt cac tcc aac      2592
Thr Leu Gly Lys Leu Gly Gln Pro Glu Phe Gly Ser Val His Ser Asn
    850                 855                 860 cag atg tct acg ccc agc aca cct act acg gag tcc aac ccc ttc aga      2640
Gln Met Ser Thr Pro Ser Thr Pro Thr Thr Glu Ser Asn Pro Phe Arg
865                 870                 875                 880 aga ctc aac tcc att agt gat atg tca tac ctt gtc aac gac agc agc      2688
Arg Leu Asn Ser Ile Ser Asp Met Ser Tyr Leu Val Asn Asp Ser Ser
                885                 890                 895 aat gag ccc ctc aga aag ggt gtc att gtt ccg gtt cag tcc ctg gaa      2736
Asn Glu Pro Leu Arg Lys Gly Val Ile Val Pro Val Gln Ser Leu Glu
            900                 905                 910 gac gcc gag gag cag ctg cct aag gcc ttg gag gca ctc cct cgt gcc      2784
Asp Ala Glu Glu Gln Leu Pro Lys Ala Leu Glu Ala Leu Pro Arg Ala
        915                 920                 925 ggg tcg aag agg aag ccg ggc gag aac ggg ctg att gca gac ctg agg      2832
Gly Ser Lys Arg Lys Pro Gly Glu Asn Gly Leu Ile Ala Asp Leu Arg
    930                 935                 940 gca agc gta cca gcc cct cgc att gag tcg aca att gaa ttg acc ggt      2880
Ala Ser Val Pro Ala Pro Arg Ile Glu Ser Thr Ile Glu Leu Thr Gly
945                 950                 955                 960 gtc tgc aac gtg gct gtc cgt gac ctc gaa gat ctt gac gac aac cag      2928
Val Cys Asn Val Ala Val Arg Asp Leu Glu Asp Leu Asp Asp Asn Gln
                965                 970                 975 atc gtt gcc cag atc aac acc att ctt gcc ggc ctc agg gac gag ttg      2976
Ile Val Ala Gln Ile Asn Thr Ile Leu Ala Gly Leu Arg Asp Glu Leu
            980                 985                 990 ctc gct cgc cgc gtc cgc cgc gtg acc ttc att tgc ggc aag gac ggc      3024
Leu Ala Arg Arg Val Arg Arg Val Thr Phe Ile Cys Gly Lys Asp Gly
        995                 1000                1005 agc tac cct ggc tac ttc acc ttc cgt gga cct acc tac gag gaa gat      3072
Ser Tyr Pro Gly Tyr Phe Thr Phe Arg Gly Pro Thr Tyr Glu Glu Asp
    1010                1015                1020 gag agc atc cgt cac agc gaa cct gcg ctc gcc ttc cag ctt gaa ctc      3120
Glu Ser Ile Arg His Ser Glu Pro Ala Leu Ala Phe Gln Leu Glu Leu
1025                1030                1035                1040 gga cgt ctg tcc aaa ttc aag atc aag ccc gtc ttc acc gag aac cgg      3168
Gly Arg Leu Ser Lys Phe Lys Ile Lys Pro Val Phe Thr Glu Asn Arg
                1045                1050                1055 aac atc cac gtc tac gag gcc atc ggc aag ggc ccc gag aac gac aac      3216
Asn Ile His Val Tyr Glu Ala Ile Gly Lys Gly Pro Glu Asn Asp Asn
            1060                1065                1070 gct gtc gac aag cgt tac ttc gtc cgt gct gtg gtg cgc ccg ggc cgt      3264
Ala Val Asp Lys Arg Tyr Phe Val Arg Ala Val Val Arg Pro Gly Arg
        1075                1080                1085 ctc cgt gac gat att ccc acc gcg gag tac ctc atc tcc gag gct gac      3312
Leu Arg Asp Asp Ile Pro Thr Ala Glu Tyr Leu Ile Ser Glu Ala Asp
    1090                1095                1100
```

-continued

| | |
|---|---|
| cgt ctc atg aat gac att ctg gat gcc ctg gag atc atc ggc aac aac<br>Arg Leu Met Asn Asp Ile Leu Asp Ala Leu Glu Ile Ile Gly Asn Asn<br>1105                      1110                   1115                   1120 | 3360 |
| aat tct gat ccg aac cac atc ttc atc aac ttc tcg ccg gtg ttc aac<br>Asn Ser Asp Pro Asn His Ile Phe Ile Asn Phe Ser Pro Val Phe Asn<br>             1125                   1130                   1135 | 3408 |
| ctg cag ccc cag gat gtg gaa gag gcc ttg gcc ggt ttc ctt gag cgc<br>Leu Gln Pro Gln Asp Val Glu Glu Ala Leu Ala Gly Phe Leu Glu Arg<br>             1140                   1145                   1150 | 3456 |
| ttc ggt cgc cgt ctc tgg cgt ctc cgt gtc acc ggt gcc gag atc cgt<br>Phe Gly Arg Arg Leu Trp Arg Leu Arg Val Thr Gly Ala Glu Ile Arg<br>         1155                   1160                   1165 | 3504 |
| att cta tgc acc gat cct gcc act ggc atg cct tat cct ctg cgt gtg<br>Ile Leu Cys Thr Asp Pro Ala Thr Gly Met Pro Tyr Pro Leu Arg Val<br>        1170                   1175                   1180 | 3552 |
| atc atc acc aac acc tac ggc ttc atc atc cag gtt gag ctg tgc att<br>Ile Ile Thr Asn Thr Tyr Gly Phe Ile Ile Gln Val Glu Leu Cys Ile<br>1185                      1190                   1195                   1200 | 3600 |
| gag aag aag tcc gag aag ggc gag tgg ctc ctc cac agc atc ggt ggt<br>Glu Lys Lys Ser Glu Lys Gly Glu Trp Leu Leu His Ser Ile Gly Gly<br>             1205                   1210                   1215 | 3648 |
| acc aac aag ctc ggc tcg atg cac ctg cgt cct gtc tcc aca ccc tac<br>Thr Asn Lys Leu Gly Ser Met His Leu Arg Pro Val Ser Thr Pro Tyr<br>        1220                   1225                   1230 | 3696 |
| ccg acc aag gag tgg ctt cag ccc aag cgt tac aag gct cat gtt atg<br>Pro Thr Lys Glu Trp Leu Gln Pro Lys Arg Tyr Lys Ala His Val Met<br>1235                      1240                   1245 | 3744 |
| ggc acc caa tac gtc tac gat ttc ccc gaa ttg ttc cga cag gcc ttc<br>Gly Thr Gln Tyr Val Tyr Asp Phe Pro Glu Leu Phe Arg Gln Ala Phe<br>             1250                   1255                   1260 | 3792 |
| cag aac agc tgg gcc aag gct gta gcc aag atc ccc tcc ctg gcc agc<br>Gln Asn Ser Trp Ala Lys Ala Val Ala Lys Ile Pro Ser Leu Ala Ser<br>1265                      1270                   1275                   1280 | 3840 |
| aag cgg ccc gcg gtt ggc gac tgc att gag tac agc gag ctt gtt ctc<br>Lys Arg Pro Ala Val Gly Asp Cys Ile Glu Tyr Ser Glu Leu Val Leu<br>             1285                   1290                   1295 | 3888 |
| gat gat acc gac aac ctg atc gaa atc tcg aga ggc cca ggt acc aac<br>Asp Asp Thr Asp Asn Leu Ile Glu Ile Ser Arg Gly Pro Gly Thr Asn<br>        1300                   1305                   1310 | 3936 |
| acc cac ggt atg gtt gga tgg atc gtt acc gct cgc acc cca gag tat<br>Thr His Gly Met Val Gly Trp Ile Val Thr Ala Arg Thr Pro Glu Tyr<br>1315                      1320                   1325 | 3984 |
| ccc gaa ggc cga cgg ttc atc atc gtt gcc aac gac atc acc ttc cag<br>Pro Glu Gly Arg Arg Phe Ile Ile Val Ala Asn Asp Ile Thr Phe Gln<br>             1330                   1335                   1340 | 4032 |
| atc ggt tcc ttc ggt ccc cag gag gac aag ttc ttc tac aag tgt acc<br>Ile Gly Ser Phe Gly Pro Gln Glu Asp Lys Phe Phe Tyr Lys Cys Thr<br>1345                      1350                   1355                   1360 | 4080 |
| gag ttg gcc agg aag ctt gga atc cct cgt atc tac ctc tca gcc aac<br>Glu Leu Ala Arg Lys Leu Gly Ile Pro Arg Ile Tyr Leu Ser Ala Asn<br>             1365                   1370                   1375 | 4128 |
| tcc ggt gct cgc atc ggt atg gcc gac gag ctg atc ccc tac ttc tcc<br>Ser Gly Ala Arg Ile Gly Met Ala Asp Glu Leu Ile Pro Tyr Phe Ser<br>        1380                   1385                   1390 | 4176 |
| gtg gct tgg aac gac ccc cag aag ccc gag gct gga ttc aag tac ctt<br>Val Ala Trp Asn Asp Pro Gln Lys Pro Glu Ala Gly Phe Lys Tyr Leu<br>             1395                   1400                   1405 | 4224 |
| tac ctc act ccc gag gtc aag caa aaa ttc gat gcc agt aag aag aag<br>Tyr Leu Thr Pro Glu Val Lys Gln Lys Phe Asp Ala Ser Lys Lys Lys<br>        1410                   1415                   1420 | 4272 |

```
gag gtc att act gag ctc att cac gat gag ggc gaa gag cgc cac aag    4320
Glu Val Ile Thr Glu Leu Ile His Asp Glu Gly Glu Glu Arg His Lys
1425                1430                1435                1440 att acg act atc att ggt gct aaa gat ggc ctg ggt gtt gag tgt ctg    4368
Ile Thr Thr Ile Ile Gly Ala Lys Asp Gly Leu Gly Val Glu Cys Leu
                1445                1450                1455 aag ggc tct ggc ctc atc gcc gga gct acc tcg cgc gct tac gag gac    4416
Lys Gly Ser Gly Leu Ile Ala Gly Ala Thr Ser Arg Ala Tyr Glu Asp
1460                1465                1470 atc ttc acc atc acc ctg gtc acc tgc cgc tcc gtt ggt att ggt gcc    4464
Ile Phe Thr Ile Thr Leu Val Thr Cys Arg Ser Val Gly Ile Gly Ala
    1475                1480                1485 tac ctt gtc cgt ctg ggc cag aga gcc atc caa gta gaa ggc cag ccg    4512
Tyr Leu Val Arg Leu Gly Gln Arg Ala Ile Gln Val Glu Gly Gln Pro
1490                1495                1500 att att ctg act ggt gcc ccg gcc atc aac aag ctg ttg ggt cgc gag    4560
Ile Ile Leu Thr Gly Ala Pro Ala Ile Asn Lys Leu Leu Gly Arg Glu
1505                1510                1515                1520 gtt tac aca tct aac ctt cag ctc ggt ggt act cag atc atg tac aag    4608
Val Tyr Thr Ser Asn Leu Gln Leu Gly Gly Thr Gln Ile Met Tyr Lys
                1525                1530                1535 aac ggt gtc tct cac atg act gcc acc gat gac ttt gag ggg tgt cag    4656
Asn Gly Val Ser His Met Thr Ala Thr Asp Asp Phe Glu Gly Cys Gln
                1540                1545                1550 aag att gtt gag tgg atg tcc ttc gtt ccc gac aag aag ggt gca tcc    4704
Lys Ile Val Glu Trp Met Ser Phe Val Pro Asp Lys Lys Gly Ala Ser
            1555                1560                1565 att ccc atc ctg ccc tgg tcc gat gac tgg gac ccg cga tgt cgc cta    4752
Ile Pro Ile Leu Pro Trp Ser Asp Asp Trp Asp Pro Arg Cys Arg Leu
    1570                1575                1580 cta ccc tct tct aag cag gct tac gat gtc cgc tgg ctc atc gct ggt    4800
Leu Pro Ser Ser Lys Gln Ala Tyr Asp Val Arg Trp Leu Ile Ala Gly
1585                1590                1595                1600 aaa aag gat gag gaa ggc ttc ctc cct ggt ctg ttc gat gcc gga tcc    4848
Lys Lys Asp Glu Glu Gly Phe Leu Pro Gly Leu Phe Asp Ala Gly Ser
                1605                1610                1615 ttt gag gag gct ctt ggt gga tgg gct cgt acc gtt gtc gtt ggt cgt    4896
Phe Glu Glu Ala Leu Gly Gly Trp Ala Arg Thr Val Val Val Gly Arg
                1620                1625                1630 gct cgc ctt ggt ggc atc cct atg ggt gta att gct gtc gag act cgt    4944
Ala Arg Leu Gly Gly Ile Pro Met Gly Val Ile Ala Val Glu Thr Arg
            1635                1640                1645 tcg gtt gag aac gtt acc cct gcc gac cct gcc aac cct gac tcc atg    4992
Ser Val Glu Asn Val Thr Pro Ala Asp Pro Ala Asn Pro Asp Ser Met
1650                1655                1660 gag gtg atc agc cag gaa gcc ggt ggt gtg tgg tac cca aac tcg gcc    5040
Glu Val Ile Ser Gln Glu Ala Gly Gly Val Trp Tyr Pro Asn Ser Ala
1665                1670                1675                1680 ttc aag acc gct cag gcc ctc cgc gac ttc aat aat ggc gag cag ctg    5088
Phe Lys Thr Ala Gln Ala Leu Arg Asp Phe Asn Asn Gly Glu Gln Leu
                1685                1690                1695 ccc gtc atg att ctg gcc aac tgg aga ggc ttc tcc ggt ggc cag cgt    5136
Pro Val Met Ile Leu Ala Asn Trp Arg Gly Phe Ser Gly Gly Gln Arg
                1700                1705                1710 gac atg tac aac gag gtt ctc aag tac ggt tcc tac atc gtc gat gct    5184
Asp Met Tyr Asn Glu Val Leu Lys Tyr Gly Ser Tyr Ile Val Asp Ala
            1715                1720                1725 ctg gtc aag tac gag cag ccc atc ttc gtt tat atc cca cct ttc ggt    5232
Leu Val Lys Tyr Glu Gln Pro Ile Phe Val Tyr Ile Pro Pro Phe Gly
```

-continued

```
         1730                 1735                 1740
gaa ctt cgt ggt ggt tca tgg gtc gtc att gat ccc acg atc aac cct   5280
Glu Leu Arg Gly Gly Ser Trp Val Val Ile Asp Pro Thr Ile Asn Pro
1745                 1750                 1755                 1760 gac cag atg gag atg tac gct gat gag gag gct cgc ggt ggt gtc ctc   5328
Asp Gln Met Glu Met Tyr Ala Asp Glu Glu Ala Arg Gly Gly Val Leu
         1765                 1770                 1775 gaa cca gaa ggt atc gtg aac atc aag tac cgc cgt gag aag cag ctc   5376
Glu Pro Glu Gly Ile Val Asn Ile Lys Tyr Arg Arg Glu Lys Gln Leu
         1780                 1785                 1790 gac act atg gct cgt ctc gac gcc acg tac ggc gag ctc cgt cgt gct   5424
Asp Thr Met Ala Arg Leu Asp Ala Thr Tyr Gly Glu Leu Arg Arg Ala
         1795                 1800                 1805 ctt gag gac cca tcc ctc agc aag gag cag ctc tca gag atc aag gcc   5472
Leu Glu Asp Pro Ser Leu Ser Lys Glu Gln Leu Ser Glu Ile Lys Ala
         1810                 1815                 1820 aag atg gcc gct cgc gaa gag cag ctc ctc cct gtc tac ctg cag atc   5520
Lys Met Ala Ala Arg Glu Glu Gln Leu Leu Pro Val Tyr Leu Gln Ile
1825                 1830                 1835                 1840 gct ctg caa ttt gct gat ctt cac gac cgc gct ggc cgc atg gtg gcc   5568
Ala Leu Gln Phe Ala Asp Leu His Asp Arg Ala Gly Arg Met Val Ala
         1845                 1850                 1855 aag aat acc atc cgc aag gcc ctg acc tgg aag aac gcc aga cgc ttc   5616
Lys Asn Thr Ile Arg Lys Ala Leu Thr Trp Lys Asn Ala Arg Arg Phe
         1860                 1865                 1870 ttc tac tgg cgt gta cgc cgc cgc ttg agc gag gag ctc att ctc aag   5664
Phe Tyr Trp Arg Val Arg Arg Arg Leu Ser Glu Glu Leu Ile Leu Lys
         1875                 1880                 1885 cgc atg gcc tct gcc gcc ccg gcc gcc gtc tcc ggc gag gcc acc ggc   5712
Arg Met Ala Ser Ala Ala Pro Ala Ala Val Ser Gly Glu Ala Thr Gly
         1890                 1895                 1900 gcc atc cct gcc acc gga ctc gtc gac ggc cag acc cca tcc aat gag   5760
Ala Ile Pro Ala Thr Gly Leu Val Asp Gly Gln Thr Pro Ser Asn Glu
1905                 1910                 1915                 1920 agc cct cgc gct aag cac ctg cgc acc ctg cac tcg tgg acc ggc ttc   5808
Ser Pro Arg Ala Lys His Leu Arg Thr Leu His Ser Trp Thr Gly Phe
         1925                 1930                 1935 ctg gac gag gaa ctc gag cac gac gac cgc aag gta gcc atg tgg tac   5856
Leu Asp Glu Glu Leu Glu His Asp Asp Arg Lys Val Ala Met Trp Tyr
         1940                 1945                 1950 gag gag aac aga aag gcc atc cag atg aag atc gag gcc ctt aag acc   5904
Glu Glu Asn Arg Lys Ala Ile Gln Met Lys Ile Glu Ala Leu Lys Thr
         1955                 1960                 1965 gac tct gtc gcc acc gag atc gcc cag ctg ctc atc agc aac aag gag   5952
Asp Ser Val Ala Thr Glu Ile Ala Gln Leu Leu Ile Ser Asn Lys Glu
         1970                 1975                 1980 ggc ggt ctc aag ggt gtg cag caa gtt ctc agc atg ctg cct gtg agg   6000
Gly Gly Leu Lys Gly Val Gln Gln Val Leu Ser Met Leu Pro Val Arg
1985                 1990                 1995                 2000 aga agg agc ccg gtg ctc aag tac ctt ggg ctc acc atg aaa ata gaa   6048
Arg Arg Ser Pro Val Leu Lys Tyr Leu Gly Leu Thr Met Lys Ile Glu
         2005                 2010                 2015 tgaaacatag aaccgccccg gtgcatatct tttgttcccc cccccccttt actggattat   6108
attttccaaa ttcctgatca cattacggta cattgaagat ggctttatac aaggcgggtg   6168
cgttagggtc tgtgttttgt ttgtctgcac tacggttttg cgttttttgtc ttgcatgggt   6228 cttggaggtt gcatcggctg attactattg tatgcattat gttggtatgc ctgatgttct   6288
ctggcaatgt ttctattcac ttttttcctag caatgccaat gaatcttcga cttcaaaaaa   6348
```
aaaaaaaaaa a                                                                          6359

<210> SEQ ID NO 2
<211> LENGTH: 2016
<212> TYPE: PRT
<213> ORGANISM: Aspergillus fumigatus

<400> SEQUENCE: 2

Asp Phe Ile Met Lys Leu Ala Gly Asn Ala Arg His Leu Glu Val Gln
 1               5                  10                  15

Leu Leu Ala Asp Gln Tyr Gly Asn Asn Ile Ser Leu Phe Gly Arg Asp
                20                  25                  30

Cys Ser Val Gln Arg Arg His Gln Lys Ile Ile Glu Glu Ala Pro Val
            35                  40                  45

Thr Ile Ala Lys Pro Ala Thr Phe Gln Ala Met Glu Arg Ala Ala Val
        50                  55                  60

Ser Leu Gly Lys Leu Val Gly Tyr Val Ser Ala Gly Thr Val Glu Tyr
 65                  70                  75                  80

Leu Tyr Ser His Ala Asp Asp Lys Phe Tyr Phe Leu Glu Leu Asn Pro
                85                  90                  95

Arg Leu Gln Val Glu His Pro Thr Thr Glu Met Val Ser Gly Val Asn
                100                 105                 110

Leu Pro Ala Ala Gln Leu Gln Ile Ala Met Gly Ile Pro Leu His Arg
            115                 120                 125

Ile Arg Asp Ile Arg Leu Leu Tyr Gly Val Asp Pro Asn Thr Ser Ser
        130                 135                 140

Glu Ile Asp Phe Asp Phe Ser Glu Glu Ser Phe Lys Thr Gln Arg
145                 150                 155                 160

Arg Pro Gln Pro Lys Gly His Thr Thr Ala Cys Arg Ile Thr Ser Glu
                165                 170                 175

Asp Pro Gly Glu Gly Phe Lys Pro Ser Ser Gly Thr Met His Glu Leu
            180                 185                 190

Asn Phe Arg Ser Ser Ser Asn Val Trp Gly Tyr Phe Ser Val Gly Thr
        195                 200                 205

Ala Gly Gly Ile His Ser Phe Ser Asp Ser Gln Phe Gly His Ile Phe
    210                 215                 220

Ala Tyr Gly Glu Thr Arg Ser Ala Ser Arg Lys His Met Val Val Ala
225                 230                 235                 240

Leu Lys Glu Leu Ser Ile Arg Gly Asp Phe Arg Thr Val Glu Tyr
                245                 250                 255

Leu Ile Lys Leu Leu Glu Thr Pro Ala Phe Glu Asp Asn Thr Ile Thr
            260                 265                 270

Thr Gly Trp Leu Asp Gln Leu Ile Ser Asn Lys Leu Thr Ala Glu Arg
        275                 280                 285

Pro Asp Pro Ile Val Ala Val Leu Cys Gly Ala Val Thr Lys Ala His
    290                 295                 300

Leu Ala Ser Glu Gly Val Glu Glu Tyr Arg Lys Gly Leu Glu Lys
305                 310                 315                 320

Gly Gln Val Pro Ser Asn Asp Val Leu Lys Thr Val Phe Pro Val Asp
                325                 330                 335

Phe Ile Tyr Glu Gly Gln Arg Tyr Lys Phe Thr Ala Thr Arg Ala Gly
            340                 345                 350

Leu Asp Ser Tyr His Leu Phe Ile Asn Gly Ser Lys Cys Ser Val Gly
        355                 360                 365

-continued

Val Arg Ala Leu Ala Asp Gly Gly Leu Val Leu Leu Asn Gly Arg
    370                 375             380

Ser His Asn Val Tyr Trp Lys Glu Ala Ala Thr Arg Leu Ser
385             390             395                 400

Val Asp Gly Lys Thr Cys Leu Leu Glu Gln Glu Asn Asp Pro Thr Gln
            405                 410                 415

Leu Arg Ser Pro Ser Pro Gly Lys Leu Val Lys Phe Thr Val Glu Asn
            420             425             430

Gly Glu His Val Lys Ala Gly Gln Ala Phe Ala Glu Val Glu Val Met
        435                 440             445

Lys Met Tyr Met Pro Leu Ile Ala Gln Glu Asp Gly Ile Val Gln Leu
450                 455             460

Ile Lys Gln Pro Gly Ser Thr Leu Glu Ala Gly Asp Ile Leu Gly Ile
465             470             475             480

Leu Ala Leu Asp Asp Pro Ser Arg Val Thr His Ala Gln Pro Phe Thr
            485             490             495

Gly Gln Leu Pro Asp Leu Gly Pro Pro Gln Val Val Gly Asn Lys Pro
        500             505             510

Pro Gln Arg Phe Ser Leu Leu His Ser Ile Leu Glu Asn Ile Leu Met
    515             520             525

Gly Tyr Asp Asn Gln Val Ile Met Asn Thr Thr Leu Lys Glu Leu Val
    530             535             540

Glu Val Leu Arg Asp Pro Glu Leu Pro Tyr Gly Glu Trp Asn Ala Gln
545             550             555                 560

Ser Ser Ala Leu His Ser Arg Met Pro Gln Lys Leu Asp Ala Gln Leu
            565             570             575

Gln Ser Ile Val Asp Lys Ala His Ala Arg Lys Ala Glu Phe Pro Ala
            580             585             590

Lys Gln Leu Gln Lys Thr Ile Ser Arg Phe Ile Glu Glu Asn Val Asn
        595             600             605

Pro Ala Asp Ala Glu Ile Leu Lys Thr Thr Leu Leu Pro Leu Gln Gln
    610             615             620

Val Ile Thr Lys Tyr Met Asp Gly Leu Lys Ala His Glu Phe Asn Val
625             630             635                 640

Phe Ala Gly Leu Leu Glu Gln Tyr Tyr Lys Val Glu Ser Leu Phe Ser
            645             650             655

Gly Arg Asn Ile Arg Asp Glu Asp Ala Ile Leu Lys Leu Arg Glu Glu
            660             665             670

His Lys Asp Asp Ile Gly Ser Val Val Gln Leu Val Leu Ser His Ser
    675             680             685

Arg Ile Gly Ala Lys Asn Asn Leu Ile Leu Ala Ile Leu Ala Met Tyr
    690             695             700

Arg Pro Asn Gln Pro Gly Ala Gly Asn Val Ala Lys Tyr Phe Lys Pro
705             710             715                 720

Val Leu Lys Lys Leu Thr Glu Leu Glu Ser Arg Pro Ala Ala Lys Val
            725             730             735

Thr Leu Lys Ala Arg Glu Val Leu Ile Gln Cys Ala Leu Pro Ser Met
            740             745             750

Glu Glu Arg Met Ser Gln Met Glu Leu Ile Leu Arg Ser Ser Val Val
        755             760             765

Glu Ser Arg Tyr Gly Glu Thr Gly Trp Asp His Arg Glu Pro Glu Phe
    770             775             780

-continued

```
Ser Val Leu Lys Glu Val Val Asp Ser Lys Tyr Thr Val Phe Asp Val
785                 790                 795                 800

Leu Thr Arg Phe Phe Val His Pro Asp Pro Trp Val Thr Leu Ala Ala
                805                 810                 815

Leu Glu Val Tyr Ile Arg Arg Ala Tyr Arg Ala Tyr Thr Leu Lys Gly
                820                 825                 830

Ile Gln Tyr Tyr Pro Asp Gly Glu Val Pro Leu Val Ser Trp Asp Phe
                835                 840                 845

Thr Leu Gly Lys Leu Gly Gln Pro Glu Phe Gly Ser Val His Ser Asn
850                 855                 860

Gln Met Ser Thr Pro Ser Thr Pro Thr Thr Glu Ser Asn Pro Phe Arg
865                 870                 875                 880

Arg Leu Asn Ser Ile Ser Asp Met Ser Tyr Leu Val Asn Asp Ser Ser
                885                 890                 895

Asn Glu Pro Leu Arg Lys Gly Val Ile Val Pro Val Gln Ser Leu Glu
                900                 905                 910

Asp Ala Glu Glu Gln Leu Pro Lys Ala Leu Glu Ala Leu Pro Arg Ala
                915                 920                 925

Gly Ser Lys Arg Lys Pro Gly Glu Asn Gly Leu Ile Ala Asp Leu Arg
930                 935                 940

Ala Ser Val Pro Ala Pro Arg Ile Glu Ser Thr Ile Glu Leu Thr Gly
945                 950                 955                 960

Val Cys Asn Val Ala Val Arg Asp Leu Glu Asp Leu Asp Asp Asn Gln
                965                 970                 975

Ile Val Ala Gln Ile Asn Thr Ile Leu Ala Gly Leu Arg Asp Glu Leu
                980                 985                 990

Leu Ala Arg Arg Val Arg Arg Val Thr Phe Ile Cys Gly Lys Asp Gly
                995                 1000                1005

Ser Tyr Pro Gly Tyr Phe Thr Phe Arg Gly Pro Thr Tyr Glu Glu Asp
    1010                1015                1020

Glu Ser Ile Arg His Ser Glu Pro Ala Leu Ala Phe Gln Leu Glu Leu
1025                1030                1035                1040

Gly Arg Leu Ser Lys Phe Lys Ile Lys Pro Val Phe Thr Glu Asn Arg
                1045                1050                1055

Asn Ile His Val Tyr Glu Ala Ile Gly Lys Gly Pro Glu Asn Asp Asn
                1060                1065                1070

Ala Val Asp Lys Arg Tyr Phe Val Arg Ala Val Arg Pro Gly Arg
                1075                1080                1085

Leu Arg Asp Asp Ile Pro Thr Ala Glu Tyr Leu Ile Ser Glu Ala Asp
    1090                1095                1100

Arg Leu Met Asn Asp Ile Leu Asp Ala Leu Glu Ile Ile Gly Asn Asn
1105                1110                1115                1120

Asn Ser Asp Pro Asn His Ile Phe Ile Asn Phe Ser Pro Val Phe Asn
                1125                1130                1135

Leu Gln Pro Gln Asp Val Glu Glu Ala Leu Ala Gly Phe Leu Glu Arg
                1140                1145                1150

Phe Gly Arg Arg Leu Trp Arg Leu Arg Val Thr Gly Ala Glu Ile Arg
                1155                1160                1165

Ile Leu Cys Thr Asp Pro Ala Thr Gly Met Pro Tyr Pro Leu Arg Val
                1170                1175                1180

Ile Ile Thr Asn Thr Tyr Gly Phe Ile Ile Gln Val Glu Leu Cys Ile
1185                1190                1195                1200

Glu Lys Lys Ser Glu Lys Gly Glu Trp Leu Leu His Ser Ile Gly Gly
```

-continued

```
                1205                1210                1215
Thr Asn Lys Leu Gly Ser Met His Leu Arg Pro Val Ser Thr Pro Tyr
            1220                1225                1230
Pro Thr Lys Glu Trp Leu Gln Pro Lys Arg Tyr Lys Ala His Val Met
            1235                1240                1245
Gly Thr Gln Tyr Val Tyr Asp Phe Pro Glu Leu Phe Arg Gln Ala Phe
            1250                1255                1260
Gln Asn Ser Trp Ala Lys Ala Val Ala Lys Ile Pro Ser Leu Ala Ser
1265                1270                1275                1280
Lys Arg Pro Ala Val Gly Asp Cys Ile Glu Tyr Ser Glu Leu Val Leu
                1285                1290                1295
Asp Asp Thr Asp Asn Leu Ile Glu Ile Ser Arg Gly Pro Gly Thr Asn
            1300                1305                1310
Thr His Gly Met Val Gly Trp Ile Val Thr Ala Arg Thr Pro Glu Tyr
            1315                1320                1325
Pro Glu Gly Arg Arg Phe Ile Ile Val Ala Asn Asp Ile Thr Phe Gln
            1330                1335                1340
Ile Gly Ser Phe Gly Pro Gln Glu Asp Lys Phe Phe Tyr Lys Cys Thr
1345                1350                1355                1360
Glu Leu Ala Arg Lys Leu Gly Ile Pro Arg Ile Tyr Leu Ser Ala Asn
                1365                1370                1375
Ser Gly Ala Arg Ile Gly Met Ala Asp Glu Leu Ile Pro Tyr Phe Ser
            1380                1385                1390
Val Ala Trp Asn Asp Pro Gln Lys Pro Glu Ala Gly Phe Lys Tyr Leu
            1395                1400                1405
Tyr Leu Thr Pro Glu Val Lys Gln Lys Phe Asp Ala Ser Lys Lys Lys
            1410                1415                1420
Glu Val Ile Thr Glu Leu Ile His Asp Glu Gly Glu Arg His Lys
1425                1430                1435                1440
Ile Thr Thr Ile Ile Gly Ala Lys Asp Gly Leu Gly Val Glu Cys Leu
                1445                1450                1455
Lys Gly Ser Gly Leu Ile Ala Gly Ala Thr Ser Arg Ala Tyr Glu Asp
            1460                1465                1470
Ile Phe Thr Ile Thr Leu Val Thr Cys Arg Ser Val Gly Ile Gly Ala
            1475                1480                1485
Tyr Leu Val Arg Leu Gly Gln Arg Ala Ile Gln Val Glu Gly Gln Pro
            1490                1495                1500
Ile Ile Leu Thr Gly Ala Pro Ala Ile Asn Lys Leu Leu Gly Arg Glu
1505                1510                1515                1520
Val Tyr Thr Ser Asn Leu Gln Leu Gly Gly Thr Gln Ile Met Tyr Lys
                1525                1530                1535
Asn Gly Val Ser His Met Thr Ala Thr Asp Asp Phe Glu Gly Cys Gln
            1540                1545                1550
Lys Ile Val Glu Trp Met Ser Phe Val Pro Asp Lys Lys Gly Ala Ser
            1555                1560                1565
Ile Pro Ile Leu Pro Trp Ser Asp Asp Trp Asp Pro Arg Cys Arg Leu
            1570                1575                1580
Leu Pro Ser Ser Lys Gln Ala Tyr Asp Val Arg Trp Leu Ile Ala Gly
1585                1590                1595                1600
Lys Lys Asp Glu Glu Gly Phe Leu Pro Gly Leu Phe Asp Ala Gly Ser
                1605                1610                1615
Phe Glu Glu Ala Leu Gly Gly Trp Ala Arg Thr Val Val Gly Arg
            1620                1625                1630
```

-continued

Ala Arg Leu Gly Gly Ile Pro Met Gly Val Ile Ala Val Glu Thr Arg
            1635                1640                1645

Ser Val Glu Asn Val Thr Pro Ala Asp Pro Ala Asn Pro Asp Ser Met
    1650                1655                1660

Glu Val Ile Ser Gln Glu Ala Gly Gly Val Trp Tyr Pro Asn Ser Ala
1665                1670                1675                1680

Phe Lys Thr Ala Gln Ala Leu Arg Asp Phe Asn Asn Gly Glu Gln Leu
                1685                1690                1695

Pro Val Met Ile Leu Ala Asn Trp Arg Gly Phe Ser Gly Gly Gln Arg
                1700                1705                1710

Asp Met Tyr Asn Glu Val Leu Lys Tyr Gly Ser Tyr Ile Val Asp Ala
                1715                1720                1725

Leu Val Lys Tyr Glu Gln Pro Ile Phe Val Tyr Ile Pro Pro Phe Gly
                1730                1735                1740

Glu Leu Arg Gly Gly Ser Trp Val Val Ile Asp Pro Thr Ile Asn Pro
1745                1750                1755                1760

Asp Gln Met Glu Met Tyr Ala Asp Glu Glu Ala Arg Gly Gly Val Leu
                1765                1770                1775

Glu Pro Glu Gly Ile Val Asn Ile Lys Tyr Arg Arg Glu Lys Gln Leu
                1780                1785                1790

Asp Thr Met Ala Arg Leu Asp Ala Thr Tyr Gly Glu Leu Arg Arg Ala
                1795                1800                1805

Leu Glu Asp Pro Ser Leu Ser Lys Glu Gln Leu Ser Glu Ile Lys Ala
                1810                1815                1820

Lys Met Ala Ala Arg Glu Glu Gln Leu Leu Pro Val Tyr Leu Gln Ile
1825                1830                1835                1840

Ala Leu Gln Phe Ala Asp Leu His Asp Arg Ala Gly Arg Met Val Ala
                1845                1850                1855

Lys Asn Thr Ile Arg Lys Ala Leu Thr Trp Lys Asn Ala Arg Arg Phe
                1860                1865                1870

Phe Tyr Trp Arg Val Arg Arg Leu Ser Glu Glu Leu Ile Leu Lys
                1875                1880                1885

Arg Met Ala Ser Ala Ala Pro Ala Ala Val Ser Gly Glu Ala Thr Gly
                1890                1895                1900

Ala Ile Pro Ala Thr Gly Leu Val Asp Gly Gln Thr Pro Ser Asn Glu
1905                1910                1915                1920

Ser Pro Arg Ala Lys His Leu Arg Thr Leu His Ser Trp Thr Gly Phe
                1925                1930                1935

Leu Asp Glu Glu Leu Glu His Asp Asp Arg Lys Val Ala Met Trp Tyr
                1940                1945                1950

Glu Glu Asn Arg Lys Ala Ile Gln Met Lys Ile Glu Ala Leu Lys Thr
                1955                1960                1965

Asp Ser Val Ala Thr Glu Ile Ala Gln Leu Leu Ile Ser Asn Lys Glu
                1970                1975                1980

Gly Gly Leu Lys Gly Val Gln Gln Val Leu Ser Met Leu Pro Val Arg
1985                1990                1995                2000

Arg Arg Ser Pro Val Leu Lys Tyr Leu Gly Leu Thr Met Lys Ile Glu
                2005                2010                2015